(12) United States Patent
Martin et al.

(10) Patent No.: US 8,517,729 B2
(45) Date of Patent: Aug. 27, 2013

(54) ORAL MOUTHPIECE AND METHOD FOR THE USE THEREOF

(75) Inventors: Ruth E. Martin, London (CA); Julie Theurer, London (CA); Michael Nuttall, London (CA); Bryan Finlay, London (CA); Brandon Coultes, Ilderton (CA)

(73) Assignee: The University of Western Ontario and Trudell Medical International, London (CA)

( * ) Notice: Subject to any disclaimer, the term of this patent is extended or adjusted under 35 U.S.C. 154(b) by 114 days.

(21) Appl. No.: 13/040,058

(22) Filed: Mar. 3, 2011

(65) Prior Publication Data
US 2011/0270166 A1 Nov. 3, 2011

Related U.S. Application Data

(60) Provisional application No. 61/310,590, filed on Mar. 4, 2010, provisional application No. 61/311,145, filed on Mar. 5, 2010, provisional application No. 61/417,041, filed on Nov. 24, 2010.

(51) Int. Cl.
*A61C 17/00* (2006.01)

(52) U.S. Cl.
USPC ................................................ 433/80; 604/77

(58) Field of Classification Search
CPC ........................................................ A61C 17/00
USPC .......... 128/205.17, 207.18; 433/80; 604/77, 604/79
See application file for complete search history.

(56) References Cited

U.S. PATENT DOCUMENTS

| | | | |
|---|---|---|---|
| 2,672,143 A * | 3/1954 | Gold et al. ..................... | 433/80 |
| 3,853,105 A | 12/1974 | Kenaqy | |
| 4,071,026 A | 1/1978 | Bevins | |
| 4,170,230 A | 10/1979 | Nelson | |
| 4,572,177 A * | 2/1986 | Tiep et al. ................ | 128/205.17 |
| 4,576,190 A | 3/1986 | Youssef | |

(Continued)

FOREIGN PATENT DOCUMENTS

| CA | 2064882 A1 | 2/1991 |
|---|---|---|
| CA | 2203257 A1 | 5/1996 |

(Continued)

OTHER PUBLICATIONS

Ali, Galib N. et al., "Influence of Cold Stimulation on the Normal Pharyngeal Swallow Response", Dysphagia, 1996, vol. 11, pp. 2-8.

(Continued)

*Primary Examiner* — Nicholas Lucchesi
*Assistant Examiner* — Gerald Landry, II
(74) *Attorney, Agent, or Firm* — Brinks Hofer Gilson & Lione

(57) ABSTRACT

The present invention relates generally to an oral device, or mouthpiece, for delivering a fluid to the mouth or oropharynx of a user. In one embodiment, the oral device includes an intraoral portion, an extraoral portion, and an auxiliary support device that serves to stabilize the oral device. In various embodiments, the auxiliary support device may be configured with ear loops, a support band, a support frame and/or a support member. The intraoral portion generally includes at least one outlet port through which the fluid is delivered to the oral cavity or oropharynx. A method of dispensing a fluid using the oral device is also provided.

18 Claims, 18 Drawing Sheets

(56) References Cited

U.S. PATENT DOCUMENTS

| | | | |
|---|---|---|---|
| 4,676,774 A | 6/1987 | Semm et al. | |
| 4,679,551 A | 7/1987 | Anthony | |
| 4,773,898 A | 9/1988 | Beqouen | |
| 4,790,305 A | 12/1988 | Zoltan et al. | |
| 4,865,021 A * | 9/1989 | Siderman | 601/164 |
| 4,996,990 A | 3/1991 | Hideshima | |
| 5,066,502 A | 11/1991 | Eales | |
| 5,085,634 A | 2/1992 | Lackney | |
| 5,143,087 A | 9/1992 | Yarkony | |
| 5,147,298 A | 9/1992 | Turner et al. | |
| 5,176,151 A | 1/1993 | Harding | |
| 5,213,553 A | 5/1993 | Light | |
| 5,377,688 A | 1/1995 | Aviv et al. | |
| 5,515,860 A | 5/1996 | Aviv et al. | |
| H1557 H | 7/1996 | Joubert et al. | |
| 5,566,645 A * | 10/1996 | Cole | 119/712 |
| 5,649,540 A | 7/1997 | Alvarez et al. | |
| 5,725,564 A | 3/1998 | Freed et al. | |
| 5,735,772 A | 4/1998 | Schiavoni | |
| 5,826,570 A | 10/1998 | Goodman et al. | |
| 5,855,908 A | 1/1999 | Stanley et al. | |
| 5,884,625 A | 3/1999 | Hart | |
| 5,891,185 A | 4/1999 | Freed et al. | |
| 5,897,492 A | 4/1999 | Feller et al. | |
| 5,950,624 A | 9/1999 | Hart | |
| 5,954,673 A | 9/1999 | Stachlin et al. | |
| 5,970,978 A | 10/1999 | Aviv et al. | |
| 5,987,359 A | 11/1999 | Freed et al. | |
| 5,993,413 A | 11/1999 | Aaltonen et al. | |
| 6,036,655 A | 3/2000 | Aviv et al. | |
| D422,694 S | 4/2000 | Hill | |
| 6,104,958 A | 8/2000 | Freed et al. | |
| 6,264,058 B1 | 7/2001 | Porter et al. | |
| 6,295,988 B1 | 10/2001 | Sue | |
| 6,299,592 B1 | 10/2001 | Zander | |
| 6,355,003 B1 | 3/2002 | Aviv et al. | |
| 6,371,758 B1 | 4/2002 | Kittelsen | |
| 6,454,788 B1 | 9/2002 | Ashton | |
| 6,484,053 B2 | 11/2002 | Leelamanit et al. | |
| 6,591,140 B2 | 7/2003 | Strome et al. | |
| 6,607,549 B2 | 8/2003 | Huang | |
| 6,805,127 B1 | 10/2004 | Karasic | |
| 6,916,287 B2 | 7/2005 | Dematteis et al. | |
| 6,935,857 B1 | 8/2005 | Farrell | |
| 6,960,183 B2 | 11/2005 | Nicolette | |
| 7,021,930 B2 | 4/2006 | Schemmer et al. | |
| 7,039,468 B2 | 5/2006 | Freed et al. | |
| 7,083,548 B1 | 8/2006 | Moore et al. | |
| 7,118,377 B2 | 10/2006 | Inoue et al. | |
| 7,147,468 B2 | 12/2006 | Snyder et al. | |
| 7,238,145 B2 | 7/2007 | Robinns et al. | |
| 7,239,918 B2 | 7/2007 | Strother et al. | |
| 7,273,327 B2 | 9/2007 | Hohlbein et al. | |
| 7,357,633 B2 | 4/2008 | Mailyan | |
| 7,477,947 B2 | 1/2009 | Pines et al. | |
| 7,660,636 B2 | 2/2010 | Castel et al. | |
| 7,935,065 B2 | 5/2011 | Martin et al. | |
| 2002/0082544 A1 | 6/2002 | Thrash | |
| 2003/0015198 A1 | 1/2003 | Heeke et al. | |
| 2003/0104342 A1 | 6/2003 | Lynch et al. | |
| 2004/0000054 A1 | 1/2004 | Sommer | |
| 2004/0028676 A1 | 2/2004 | Klien et al. | |
| 2004/0138585 A1 | 7/2004 | Dematteis et al. | |
| 2005/0222535 A1 | 10/2005 | Uesugi et al. | |
| 2006/0110710 A1 | 5/2006 | Schemmer et al. | |
| 2006/0210480 A1 | 9/2006 | Hamdy | |
| 2006/0235352 A1 | 10/2006 | Dziewas | |
| 2006/0282010 A1 | 12/2006 | Martin et al. | |
| 2008/0009810 A1 | 1/2008 | Hamdy | |
| 2008/0077192 A1 | 3/2008 | Harry et al. | |
| 2008/0147141 A1 | 6/2008 | Testerman et al. | |
| 2008/0147142 A1 | 6/2008 | Testerman et al. | |
| 2008/0190436 A1 * | 8/2008 | Jaffe et al. | 128/207.18 |
| 2008/0251597 A1 | 10/2008 | Pearson | |
| 2008/0269837 A1 | 10/2008 | Ludlow et al. | |
| 2008/0269856 A1 | 10/2008 | Cross et al. | |
| 2008/0269857 A1 | 10/2008 | Cross et al. | |
| 2008/0269858 A1 | 10/2008 | Cross et al. | |
| 2008/0269859 A1 | 10/2008 | Cross et al. | |
| 2008/0269860 A1 | 10/2008 | Cross et al. | |
| 2008/0269861 A1 | 10/2008 | Cross et al. | |
| 2009/0018611 A1 | 1/2009 | Campbell et al. | |
| 2009/0048645 A1 | 2/2009 | Philipp et al. | |
| 2009/0048647 A1 | 2/2009 | Tingey | |
| 2009/0054980 A1 | 2/2009 | Ludlow et al. | |
| 2009/0120446 A1 | 5/2009 | Vaska et al. | |
| 2009/0120447 A1 | 5/2009 | Vaska et al. | |
| 2009/0123886 A1 | 5/2009 | Vaska | |
| 2009/0137859 A1 | 5/2009 | Belafsky et al. | |
| 2009/0249571 A1 | 10/2009 | Rohrig | |
| 2009/0259310 A1 | 10/2009 | Blom | |
| 2009/0286237 A1 | 11/2009 | Fitzgerald et al. | |
| 2009/0306626 A1 | 12/2009 | Sinha et al. | |
| 2009/0306741 A1 | 12/2009 | Hogle et al. | |
| 2010/0010400 A1 | 1/2010 | Martin et al. | |
| 2010/0016908 A1 * | 1/2010 | Martin et al. | 607/3 |
| 2010/0055233 A1 | 3/2010 | Macinnis et al. | |
| 2010/0121224 A1 | 5/2010 | Toyota et al. | |

FOREIGN PATENT DOCUMENTS

| | | |
|---|---|---|
| EP | 1341430 B1 | 9/2007 |
| JP | 11-309186 A | 11/1999 |
| WO | WO 90/10470 A1 | 9/1990 |
| WO | WO 96/11627 A1 | 4/1996 |
| WO | WO 00/27459 A1 | 5/2000 |
| WO | WO 02/38012 A2 | 5/2002 |
| WO | WO 03/061453 A2 | 7/2003 |
| WO | WO 2004/028433 A2 | 4/2004 |
| WO | WO 2004/028433 A3 | 4/2004 |
| WO | WO 2004/069076 A2 | 8/2004 |
| WO | WO 2004/075743 A1 | 9/2004 |
| WO | WO 2005/070316 A1 | 8/2005 |
| WO | WO 2005/102458 A2 | 11/2005 |
| WO | WO 2005/122877 A1 | 12/2005 |
| WO | WO 2006/024825 A1 | 3/2006 |
| WO | WO 2006/083217 A1 | 8/2006 |
| WO | WO 2006/106327 A1 | 10/2006 |
| WO | WO 2006/108066 A2 | 10/2006 |
| WO | WO 2006/116843 A1 | 11/2006 |
| WO | WO 2006116843 A1 * | 11/2006 |
| WO | WO 2006/108066 A3 | 12/2006 |
| WO | WO 2007/005582 A1 | 1/2007 |
| WO | WO 2007/021468 A2 | 2/2007 |
| WO | WO 2007/021468 A3 | 2/2007 |
| WO | WO 2007/022034 A2 | 2/2007 |
| WO | WO 2007/081764 A2 | 7/2007 |
| WO | WO 2007/081764 A3 | 7/2007 |
| WO | WO 2007/123746 A2 | 11/2007 |
| WO | WO 2007/123746 A3 | 11/2007 |
| WO | WO 2008/076646 A1 | 6/2008 |
| WO | WO 2009/127947 A2 | 10/2009 |
| WO | WO 2009127947 A2 * | 10/2009 |

OTHER PUBLICATIONS

Aviv, Jonathan E. et al., "Air Pulse Quantification of Supraglottic and Pharyngeal Sensation: A New Technique", Ann Otol Rhinal Laryngol, 1993, vol. 102, pp. 777-780.

Aviv, Jonathan E. et al., "Clinical assessment of Pharyngolaryngeal Sensitivity", The American Journal of Medicine, 2000, vol. 108 (4A), pp. 68S-72S.

Aviv, Jonathan E. et al., "Effects of Aging on Sensitivity of the Pharyngeal and Supraglottic Areas", The American Journal of Medicine, 1997, vol. 103 (5A), pp. 74S-76S.

Aviv, Jonathan E. et al., "Laryngopharyngeal Sensory Deficts in Patients with Laryngopharyngeal Reflux and Dysohagia", Ann Otol Rhinal Laryngol, 2000, vol. 109, pp. 1000-1006.

Aviv, Jonathan E. et al., "Laryngopharyngeal Sensory Discrimination Testing and the Laryngeal Adductor Reflex", Ann Otol Rhinal Laryngol, 1999, vol. 108, pp. 725-730.

Aviv, Jonathan E. et al., "Silent Laryngopharyngeal Sensory Deficits After Stroke", Ann Otol Rhinal Laryngol, 1997, vol. 106, pp. 87-93.

Aviv, Jonathan E. et al., "Surface sensibility of the floor of the mouth and tongue in healthy controls and in radiated patients", Annual Meeting of the American Academy of Otolaryngology—Head and Neck Surgery, Kansas City, MO., 1991, pp. 418-423.

Aviv, Jonathan E. et al., "Supraglottic and Pharyngeal sensory Abnormalities in Stroke patients with Dysphagia", Ann Otol Rhinal Laryngol, 1996, vol. 105, pp. 92-97.

Balzamo, E. et al., "Short-latency components of evokes potentials to median nerve stimulation recorded by intracerebral electrodes in the human pre- and postcentral areas", Clinical Neurophysiology, 2004, vol. 115, pp. 1616-1623.

Barberi, Enzo A. et al., "A Transmit-Only/Receive-Only (TaRO) RF System for High-Field MRIIMRS Applications", Magnetic Resonance in Medicine, 2000, vol. 43, pp. 284-289.

Beckmann, Christian F. et al., "Probabilistic Independent Component Analysis for Functional Magnetic Resonance Imaging", IEEE Transactions on medical Imaging, 2004, vol. 23, No. 2. pp. 137-152.

Bessho, H. et al., "Localization of Palatal Area in Human Somatosensory Cortex", J Dent Res, 2007, vol. 86, No. 3, pp. 265-270.

Boliek, C. E. et al., "Establishing a reliable protocol to measure tongue sensation", Journal of Oral Rehabilitation, 2007, vol. 34, pp. 433-441.

Bourdiol, P. et al., "Effect of age on salivary flow obtained under feeding and non-feeding conditions", Journal of Oral Rehabilitation, 2004, vol. 31, pp. 445-452.

Bove, Mogens et al., "Thermal Oral-Pharyngeal Stimulation and Elicitation of Swallowing", Acta Otolaryngol (Stochk), 1998, vol. 118. pp. 728-731.

Broekhuusen M. L. et al., "Factors Influencing jaw Position Sense in Man", Archs oral Biol., 1983, vol. 28, No. 5, pp. 387-391.

Calhoun, Karen K. et al., "Age-Related Changes in Oral Sensation", Laryngoscope, 1992, vol. 102, pp. 109-116.

Capra, Norman F., "Mechanism of Oral Sensation", Dysphagia, 1995, vol. 10, pp. 235-247.

Chamberlain, Cheryl K. et al., "Intra-oral tactile sensation and aging in a community-based population", Aging Clin Exp Res, 2006, vol. 19, No. 2, pp. 85-90.

Cook, I. J. et al., "Influence of aging on oral-pharyngeal bolus transit and clearance during swallowing: scintigraphic study", The American Physiological Society, 1994, pp. G972-G977.

Craig, A. D. et al., "Thermosensory activation of insular cortex", 2000, Nature Neuroscience, vol. 3, No. 2, pp. 184-190.

Dale et al. "Cortical Surface-Based Analysis", NeuroImage, 1999, vol. 9, pp. 179-194.

Darian-Smith, I. et al., "Somatic Sensory Cortical Projection Areas Excited by Tactile Stimulation of the Cat: A Triple Representation", J. Physiol., 1966, vol. 182. pp. 671-689.

Dawes, C. et al., "Circadian Rhythms in the Flow Rate and Proportional Contribution of Parotid to Whole Saliva Volume in Man", Archs oral Biol., 1973, vol. 18. pp. 1145-1153.

Dawes, C., "Circadian Rhythms in Human Salivary Flo Rate and Composition", J. Physiol., 1972, vol. 220. pp. 529-545.

Ding, Ruiying et al., "The Effects of taste and Consistency on Swallow Physiology in Younger and Older Healthy Individuals: A Surface Electromyographic Study", Journal of Speech, Language, and Hearing Research, 2003, vol. 46, pp. 977-989.

Disbrow, Elizabeth A. et al., "Ipsilateral Representation of Oral Structures in Human Anterior Parietal Somatosensory Cortex and Integration of Inputs Across the Midline", The Journal of Comparative Neurology, 2003, vol. 467, pp. 487-495.

Do, David H. et al., "Resolving Subjects and Measuring Observer/Subject Distances with a Thermal Tactile Imager", IEEE, 301 Annual International IEEE EMBS Conference, Vancouver, Canada, 2008, pp. 4302-4305.

Doty, Robert W., "Influence of Stimulus pattern on Reflex Deglutition", Dept. of Physiology, The University of Chicago, 1951, vol. 166, pp. 142-158.

Dum, Richard R. et al., "Motor areas in the frontal lobe of the primate", Physiology and Behavior, 2002, vol. 77, pp. 677-682.

Ettlin, D. A. et al., "Cortical Activation Resulting from Painless Vibrotactile Dental Stimulation Measured by Functional Magnetic Resonance Imaging (fMRI)", J. Dent Res .. 2004, vol. 83, No. 10. pp. 757-761.

Extended European Search Report for EP Application No. 06721849.5, dated Nov. 5, 2009, 10 pages.

Fabri, Mara et al., "Bilateral Cortical Representation of the Trunk Midline in Human First Somatic Sensory Area", Human Brain Mapping, 2005, vol. 25, pp. 287-296.

Ferguson D. B. et al., "Circadian Rhythms in Human Partotid Saliva Flow Rate and Composition", Archs oral Biol., 1973, vol. 18. pp. 1155-1173.

Flynn, Frederick et al., "Anatomy of the insula-functional clinical correlates", Aphasiology, 1999, vol. 13, No. 1, pp. 55-78.

Fraser, Chris et al., "Driving Plasticity in Human Adult Motor Cortex is Associated with Improved Motor Function after Brain Injury", Neuron, 2002, vol. 34, pp. 831-840.

Freed M. L. et al., "Electrical stimulation for swallowing disorders caused by stroke", Respir care, 2001, vol. 46, No. 5, p. 466.

Fujiu, Masako et al., "Glossopharyngeal evoked potentials in normal subjects following n=mechanical stimulation of the anterior faucial pillar", Electroencephalography and Clinical Neurophysiology, 1994, vol. 92, pp. 183-195.

Fukunaga, Akiko et al., "Influences of Aging on Taste Perception and Oral Somatic Sensation", Journal of Gerontology: Medical Sciences, 2005, vol. 60A, No. 1, pp. 109-113.

Gemba, Hisae et al., "Influences of emotion upon parotid secretion in human", Neuroscience Letters, 1996, vol. 211, pp. 159-162.

Gross, Roxann D. et al., "Lung Volume Effects on Pharyngeal Swallowing Physiology", J. Appl. Physiol, vol. 95, 2003, pp. 2211-2217.

Hamdy, S. et al., "Modulation of human swallowing behavior by thermal and chemical stimulation in health and after brain injury", Neurogastroenterology and Motility, 2003, vol. 15, pp. 69-77.

Hamdy, Shaheen et al., "Cranial nerve modulation of human cortical swallowing motor pathways", American Physiological Society, 1997, pp. G802-G808.

Hamdy, Shaheen et al., "Explaining oropharyngeal dysphagia after unilateral hemispheric stroke", The Lancet, 1997, vol. 350, pp. 686-692.

Hamdy, Shaheen et al., "Long-term reorganization of human motor cortex driven by short-term sensory stimulation", Nature America Inc., 1998, vol. 1, No. 1, pp. 64-68.

Hamdy, Shaheen et al., "Recovery of Swallowing After Dysphagic Stroke Relates to Functional Reorganization in the Intact Motor Cortex", Gastroenterology, 1998; vol. 115, No. 5, pp. 1104-1112.

Hamdy, Shaheen et al., "The cortical topography of human swallowing musculature in health and disease", Nature Medicine, 1996, vol. 2, No. 11, pp. 1217-1224.

Hammer, MJ, "Design of a new somatosensory stimulus delivery device for measuring laryngeal mechanosensory detection thresholds in humans," IEEE Trans Biomed Eng., Apr. 2009, vol. 56(4), pp. 1154-1159 (Abstract only).

Hayashi, H. et al., "Functional Organization of Trigeminal Subnucleus Interpolaris: Nociceptive and Innocuous Afferent Inputs, Projections to Thalamus, Cerebellum, and Spinal Cord, and Descending Modulation From Periaqueductal Gray", The American Physiological Society, Journal of Neurophysiology, 1984, vol. 51, No. 5, pp. 890-905.

Hiraba, Hisao et al. "Increased Secretion of Salivary Glands Produced by Facial Vibrotactile", Somatosensory and Motor Research, vol. 25, 2008, pp. 222-229.

Huang, C.-S. et al., "Input-Output Relationships of the Primary Face Motor Cortex in the Monkey (*Macaca fascicularis*)", The American Physiological Society, Journal of Neurophysiology, 1989, vol. 61, No. 2, pp. 350-362.

Iwamura, Yoshiaki et al., "Bilateral Activity and Callosal Connections in the Somatosensory Cortex", The Neuroscientist, 2001, vol. 7, No. 5, pp. 419-429.

Iyengar, Soumya et al., "Cortical and Thalamic Connections of the Representations of the Teeth and Tongue on Somatosensory Cortex of New World Monkeys", The Journal of Comparative Neurology, 2007, vol. 501, pp. 95-120.

Jacobs, Reinhilde et al., "Oral stereognosis: a review of the literature", Clin Oral Invest, 1998, vol. 2, pp. 3-10.
Jafari, Samah et al. "Sensory Regulation of Swallowing and Airway Protection: A Role for the Internal Superior Laryngeal Nerve in Humans", J. Physiol. Soc., vol. 550, No. 1, 2003. pp. 287-304.
Jain, Neeraj et al., "Anatomic Correlates of the face and Oral Cavity Representations in the Somatosensory Cortical Area 3b Monkeys", The Journal of Comparative Neurology, 2001, vol. 429, pp. 455-468.
Jaradeh, Safwan, MD, "Neurophysiology of Swallowing in the Aged", Dysphagia, 1994, vol. 9, pp. 218-220.
Jean, Andre et al., "Inputs to the swallowing medullary from the peripheral afferent fibers and the swallowing cortical area", Brain Research, 1979, vol. 178, pp. 567-572.
Jean, Andre, "Brain Stem Control of Swallowing: Neuronal Network and Cellular Mechanisms", The American Physiological Society, 2001, vol. 81, No. 2, pp. 929-969.
Jobin, Vincent et al., "Swallowing function and upper airway sensation in obstructive sleep apnea", J. Appl. Physio/., 2007, vol. 102, pp. 1587-1594.
Kaatzke-McDonald, Monika N., M App Sc et al., "The Effects of Cold, Touch, and Chemical Stimulation of the Anterior Faucial Pillar on Human Swallowing", Dysphagia, 1996, vol. 11, pp. 198-206.
Kapila, Yagya V., MD et al., "Relationship Between Swallow Rate and Salivary Flow", Digestive Diseases and Sciences, 1984, vol. 29, No. 6, pp. 528-533.
Kern, Mark K. et al., "Cerebral cortical representation of reflexive and volitional swallowing in humans", American Physiological Society, Am J Physiol Gastrointest Liver Physiol, 2001, vol. 280, pp. G354-G360.
Kim, Il Soo et al., "Influence of Mastication and Salivation on Swallowing in Stroke Patients", Arch Phys Med Rehabil, 2005, vol. 86, pp. 1986-1990.
Kitagawa, Jun-Ichi et al., "Pharyngeal branch of the glossopharyngeal nerve plays a major role in reflex swallowing from the pharynx", American Physiological Society, Am J Physiol Regulatory Integrative Comp Physiol, 2002, vol. 282, pp. R1342-R1347.
Kleim, Jeffrey A. et al., "Principles of Experience-Dependent Neural Plasticity: Implications for Rehabilitation After Brain Damage", Journal of Speech, Language, and Hearing Research, 2008, vol. 51, pp. S225-S239.
Laqerlof, F. et al., The Volume of Saliva in the Mouth Before and After Swallowing, Univof Western Ontario, 2009, vol. 63, No. 5, pp. 618-621.
Lazzara, Gisela de Lama, M.A. et al., "Impact of Thermal Stimulation on the Triggering of the Swallowing Reflex", Dysphagia, 1986, vol. 1, pp. 73-77.
Lear, C. S. C. et al., "The Frequency of Deglutition in Man", Arch. oral Biol., 1965, vol. 10, pp. 83-99.
Lim, Kil-Byung, MD, PhD et al., "Neuromuscular Electrical and Thermal-Tactile Stimulation for Dysphagia Caused by Stroke: A Randomized Controlled Trial", J Rehabil Med, 2009, vol. 41, pp. 174-178.
Lin, L.-D. et al., "Functional Properties of Single Neurons in the Primate Face Primary Somatosensory Cortex. II. Relations With Different Directions of Trained Tongue Protrusion", The American Physiological Society, Journal of Neurophysiology, 1994, vol. 71, No. 6, pp. 2391-2400.
Linden, Patricia, M.A. et al. "Bolus Position at Swallow Onset in Normal Adults: Preliminary Observations", Dysphagia, 1989, vol. 4, pp. 146-150.
Logemann, Jeri A. et al., "Closure mechanisms of laryngeal vestibule during swallow", The American Physiotcqicel Society, Am. J. Physiol., 1992, vol. 262, pp. G338-G344.
Logemann, Jeri A. et al., Temporal and Biomechanical Characteristics of Oropharyngeal Swallow in Younger and Older Men, American Speech Language-Hearing Association, Journal of Speech, Language, and Hearing Research, 2000, vol. 43, pp. 1264-1274.
Logemann, Jeri A., "The Effects of VitalS tim on Clinical Research Thinking in Dysphagia", Dysphagia, No. 22, 2007, pp. 11-12.
Logemann, Jeri A., Ph.D., "Preswallow Sensory Input: Its Potential Importance to Dysphagic Patients and Normal Individuals", Dysphagia, 1996, vol. 11, pp. 9-10.
Logemann, Jeri et al., "Effects of a Sour Bolus on Oropharyngeal Swallowing Measures in Patients With Neurogenic Dysphagia", Journal of Speech and Hearing Research, 1995, vol. 35, pp. 556-563.
Lowell, Soren et al., "Sensory Stimulation Activates Both Motor and Sensory Components of the Swallow System", NeuroImage, vol. 42, 2008, pp. 285-295.
Lowell, Soren et al., "The Effects of Sensory Stimulation on Urge and Frequency of Swallowing", PPT Presentation made at the 2008 meeting of the Dysphagia Research Society, National Institutes of Health, 2008, 14 pgs.
Lowell, Soren, Abstract, entitled "Cerebral activation patterns during swallowing and related tasks using functional magnetic resonance imaging," Dysphagia, vol. 22, 2007, pp. 401, 2 pages.
Malenfant, Annie et al., "Tactile, thermal and pain sensibility in burned patients with and without chronic pain and paresthesia problems", International Association for the Study of Pain, 1998, vol. 77, pp. 241-251.
Manger, Paul R. et al., "Representation of Face and Intra-Oral Structures in Area 3b of Macaque Monkey Somatosensory Cortex", The Journal of Comparative Nurology, 1996, vol. 371, pp. 513-521.
Mansson, Ingemar, MD. et al., "Effects of Surface Anesthesia on Deglutition in Man", Department of Otorhinolaryngology, University of Gothenburg, Sweden, 1973-1974, pp. 427-437.
Marik, Paul E., MD, FCCP et al., "Aspiration Pneumonia and Dysphagia in the Elderly", American College of Chest Physicians, CHEST, 2003, vol. 124, pp. 328-336.
Martin, Ruth E. et al., "Cerebral Areas Processing Swallowing and Tongue Movement are Overlapping but Distinct: A Functional Magnetic Resonance Imaging Study", The American Physiological Society, J Neurophysiol, 2004, vol. 92, pp. 2428-2443.
Martin, Ruth E. et al., "Cerebral Cortical Representation of Automatic and Volitional Swallowing in Humans", The American Physiological Society, J Neurophysiol, 2001, vol. 85, pp. 938-950, www.jn.physiology.org.
Martin, Ruth E. et al., "Features of Cortically Evoked Swallowing in the Awake Primate (*Macaca fascicularis*)", The American Physiological Society, J. Neurophysiol., 1999, vol. 82, pp. 1529-1541.
Martin, Ruth E. et al., "The Role of the Cerebral Cortex in Swallowing", Dysphagia, 1993, vol. 8, pp. 195-202.
Martin, Ruth E. et al., "Functional Properties of Neurons in the Primate Tongue Primary Motor Cortex During Swallowing", The American Physiological Society, 2007, pp. 1516-1530.
Martin, Ruth E., "Neuroplasticity and Swallowing", Dysphagia, 2008, 12 pages.
Martin, Ruth et al., "Cerebral cortical processing of swallowing in older adults", Exp Brain Res, 2007, vol. 176, pp. 12-22.
McKee, G. J. et al., "Does age or sex affect pharyngeal swallowing?", Clinical Otolaryngology, 1998, vol. 23, pp. 100-106.
Menon, Ravi S., "Postacquisition Suppression of Large-Vessel Bold Signals in High-Resolution fMRI", Magnetic Resonance in Medicine, 2002, vol. 47, pp. 1-9.
Mese, H. et al., "Invited Review—Salivary secretion, taste and hyposalivation", Journal of Oral Rehabilitation, 2007, vol. 34, pp. 711-723.
Miller, Arthur J., "Deslution", Physiological Reviews, 1982. vol. 62, No. 1, pp. 129-184.
Miyamoto, Jun J. et al., "The Representation of the Human Oral Area in the Somatosensory Cortex: a Functional MRI Study", Cerebral Cortex, 2006, vol. 16, No. 5, pp. 669-675.
Mizobuchi, Keiko et al., "Single unit responses of human cutaneous mechanoreceptors to air-puff stimulation", Clinical Neurophysiology, 2000, vol. 111, pp. 1577-1581.
Mosier, Kristine, DMD, PhD et al., "Cortical Representation of Swallowing in Normal Adults: Functional Implications", The American Laryngological, Rhinological and Otological Society, Inc., The Laryngoscope, 1999, vol. 109, pp. 1417-1423.
Mu, Liancai et al., "Sensory Nerve Supply of the Human Oro- and Laryngopharynx: A Preliminary Study", The Anatomical Record, 2000, vol. 258, pp. 406-420.
Murray, Joseph et al., "The Significance of Accumulated Oropharyngeal Secretions and Swallowing Frequency in Predicting Aspiration", Dysphagia, 1996, vol. 11, pp. 99-103.

Nakamura, Akinori et al., "Somatosensory Homunculus as Drawn by MEG", NeuroImage, 1998, vol. 7, pp. 377-386, Article No. N1980332.

Navazesh, M. et al., "A Comparison of Whole Mouth Resting and Stimulated Salivary Measurement Procedures", J Dent Res, 1982, vol. 61, No. 10, pp. 1158-1162.

Nguyen, Anh Tu et al., "Laryngeal and Velopharyngeal Sensory Impairment in Obstructive Sleep Apnea", SLEEP, 2005, vol. 28, No. 5, pp. 585-593.

Office Action from U.S. Appl. No. 11/411,241, dated Nov. 13, 2009, 9 pages.

Office Action from Chinese Application No. 200680014928.9, dated Mar. 6, 2009, 5 pages.

Office Action in Chinese Application No. 200680014928.9, dated Nov. 27, 2009, 6 pages.

Ootani, Shinji et al., "Convergence of Afferents from the SLN and GPN in Cat Medullary Swallowing Neurons", Brain Research Bulletin, 1995, vol. 37, No. 4, pp. 397-404.

Palmer, Jeffrey B., M.D. et al., "Coordination of Mastication and Swallowing", Dysphagia, 1992, vol. 7, pp. 187-200.

Pentax, ENT Scopes, Product brochure, 2005, 2 pgs.

Pommerenke, W. T., "A Study of the Sensory Areas Eliciting the Swallowing Reflex", The American Journal of Physiology, 1927, vol. 81, No. 1, pp. 36-41.

Power, M. et al., "Changes in pharyngeal corticobulbar excitability and swallowing behavior after oral stimulation", Am J. Physiol Garstrointest Liver Physiol, 2004, vol. 286 pp. G45-G50.

Power, Macine L., PhD et al., "Evaluating Oral Stimulation as a Treatment for Dysphagia after Stroke", Dysphagia, 2006, pp. 49-55.

Program of the 103rd Meeting of the Acoustical Society of America, J. Acoust. Am., 1982, Suppl. 1, vol. 71 pp. S1-S113.

Robbins, JoAnne et al., "Swallowing After Unilateral Stroke of the Cerebral Cortex Preliminary Experience", Dysphagia, 1988, vol. 3, pp. 11-17.

Robbins, JoAnne et al., "Swallowing and Dysphagia Rehabilitation: Translating Principles of Neural Plasticity Into Clinically Oriented Evidence", American Speech-Language-Hearing Association, Journal of Speech, Language, and Hearing Research, 2008, vol. 51, pp. S276-S300.

Rosenbeck, John C. et al., "Effects of Thermal Application on Dysphagia After Stroke", Journal of Speech and Hearing Research, 1991, vol. 34, pp. 1257-1268.

Rosenbek, John C., PhD et al., "Comparing Treatment Intensities of Tactile-Thermal Application", Dysphagia, 1998, vol. 13, pp. 1-9.

Rosenbek, John C., PhD et al., "Thermal Application Reduces the Duration of Stage Transition in Dysphagia after Stroke", Dysphagia, 1996, vol. 11, pp. 225-233.

Ruben, J. et al., "Somatotopic Organization of Human Secondary Somatosensory Cortex", Cerebral Cortex, 2001, vol. 11, No. 5, pp. 463-473.

Rudney, J. D. et al., "The Prediction of Saliva Swallowing Frequency in Humans From Estimates of Salivary Flow Rate and the Volume of Saliva Swallowed", Archs oral Biol., 1995, vol. 40, No. 6, pp. 507-512.

Schneyer, Leon H. et al., "Rate of Flow of Human Parotid, Sublingual, and Submaxillary Secretions During Sleep", J. D. Res., 1956, vol. 35, No. 1, pp. 109-114.

Sciortino, Kellie Filter, PhD, CCC-SLP et al., "Effects of Mechanical, Cold, Gustatory, and Combined Stimulation to the Human Anterior Faucial Pillars", Dysphagia, 2003, vol. 18, pp. 16-26.

Servos, Philip et al., "fMRI evidence for an inverted face representation in human somatosensory cortex", NeuroReport, 1999, vol. 10, No. 7, pp. 1393-1395.

Sessle, B. J., "Review Article, Mechanisms of oral somatosensory and motor functions and their clinical correlates", Journal of Oral Rehabilitation, 2006, vol. 33, pp. 243-261.

Sessle. Barry J. et al., "Cortical mechanisms controlling mastication and swallowing in the awake monkey", Brain and oral Functions, Published by Elsevier Science B.v. 1995, pp. 181-189.

Shaffer, Scott W. et al., "Aging of the Somatosensory System: A translational Perspective", American Physical Therapy Association, 2007, vol. 87, No. 2, pp. 193-207.

Shaw, D. W. et al., "Influence of normal aging on oral-pharyngeal and upper esophageal sphincter function during swallowing", American Physiological Society, Am. J. Physiol., 1995, vol. 268, pp. G389-G396.

Ship, Jonathan A., DMD et al., "Xerostomia and the Geriatric Patient", Journal of American Geriatric Society, 2002, vol. 50, No. 3, pp. 535-543.

Simon, Sidney A. et al., "The neural mechanisms of gestation: a distributed processing code", Nature Reviews, Neuroscience, 2006, vol. 7, pp. 890-901.

Sinclair, William J., "Role of the pharyngeal plexus in initiation of swallowing", American Journal of Physiology, 1971, vol. 221, No. 5, pp. 1260-1263.

Smith, Stephen M., "Fast Robust Automated Brain Extraction", Human Brain Mapping, 2002, vol. 17, pp. 143-155.

Sonies, Barbara C., Ph.D. et al., "Durational Aspects of the Oral-Pharyngeal Phase of Swallow in Normal Adults", Dysphagia, 1988, vol. 3, pp. 1-10.

Söros, P. et al., "Functional MRI of Oropharyngeal Air-Pulse Stimulation", Neuroscience, 2008, vol. 153, pp. 1300-1308.

Söros, Peter et al., "Functional MRI of working memory and selective attention in vibrotactile frequency discrimination", BMC Neuroscience, 2007, vol. 8, No. 48, pp. 1-10.

Söros, Peter et al., "Clustered functional MRI of overt speech production", NeuroImage, 2006, vol. 32, pp. 376-387.

Stephen, Jennifer R., MSc et al., "Bolus Location at the Initiation of the Pharyngeal Stage of Swallowing in Healthy Older Adults", Dysphagia, 2005, vol. 20, pp. 266-272.

Tanji, J. et al., "Submodality Distribution in Sensorimotor Cortex of the Unanesthetized Monkey", Journal of Neurophysiology, 1981, vol. 45, No. 3, pp. 467-481.

Taoka, Miki et al., "Representation of the midline trunk, bilateral arms, and shoulders in the monkey postcentral somatosensory cortex", Exp Brain Res, 1998, vol. 123, pp. 315-322.

Theurer, Julie A., MCISc et al., "Oropharyngeal Stimulation with Air-Pulse Trains Increases Swallowing Frequency in Healthy Adults", Dysphagia, 2005, vol. 20, pp. 254-260.

Theurer, Julie et al. "The Effects of Oropharyngeal Air-Pulse Stimulation on Swallowing in Healthy Older Adults", Dysphagia, 2009, 12 pgs.

Tracy, Julie F., M.A. et al., "Preliminary Observations on the Effects of Age on Oropharyngeal Deglutition", Dysphagia, 1989, vol. 4, pp. 90-94.

Van Willigen, J. D. et al., "On the Self-Perception of Jaw Positions in Man", Archs oral Biol., 1983, vol. 28, No. 2, pp. 117-122.

Vandenbergh, Joris et al., "Regional Brain Activation During Proximal Stomach Distention in Humans: A Positron Emission Tomography Study", American Gastroenterological Association, 2005, vol. 128, pp. 564-573.

Woolrich, Mark W. et al., "Multilevel linear modeling for FMRI group analysis using Bayesian inference", NeuroImage, 2004, vol. 21, pp. 1732-1747.

Yamamoto, Takashi et al., "Taste Responses of Cortical Neurons in Freely Ingesting Rats", Journal of Neurophysiology, 1989, vol. 61, No. 6, pp. 1244-1258.

Yamashita, H. et al., "Magnetic sensory cortical responses evoked by tactile stimulations of the human face, oral cavity and flap reconstructions of the tongue", Eur Arch Otorhinolaryngol, 1999, vol. 256, pp. S42-S46.

Yoshida, Kazuya et al., "Somatosensory evoked magnetic fields to air-puff stimulation on the soft palate", Neuroscience Research, 2006, vol. 55, pp. 116-122.

Yoshida, Yoshikazu, MD et al., "Sensory Innervation of the Pharynx and Larynx", The American Journal of Medicine, 2000, vol. 108 (4A), pp. 51 S-61 S.

Zald, David H. et al., "Cortical Activation Induced by Intraoral Stimulation with Water in Humans", Chern. Senses, 2000, vol. 25, pp. 267-275.

International Search Report for International Application No. PCT/CA2006/000650, dated Sep. 6, 2006, 2 pages.

International Search Report for International Application No. PCT/IB2009/005252, dated Oct. 7, 2006, 5 pages.
International Search Report for International Application No. PCT/IB2011/000443, dated Aug. 3, 2011, 2 pages.
Written Opinion of the International Searching Authority for International Application No. PCT/IB2011/000443, dated Aug. 3, 2011, 7 pages.

International Search Report for International Application No. PCT/IB2011/000450, dated Aug. 15, 2011, 3 pages.
Written Opinion of the International Searching Authority for International Application No. PCT/IB2011/000450, dated Aug. 15, 2011, 7 pages.

* cited by examiner

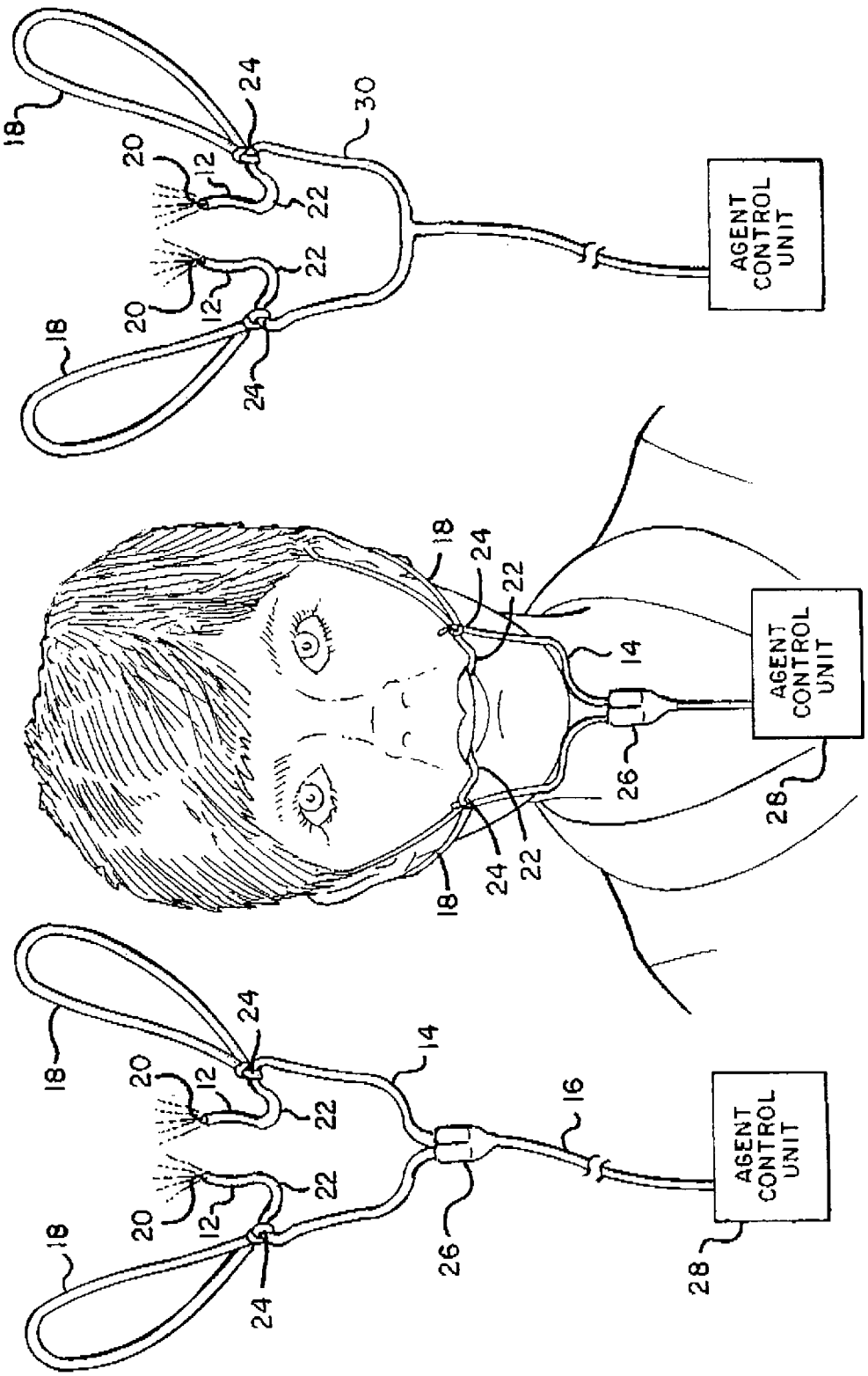

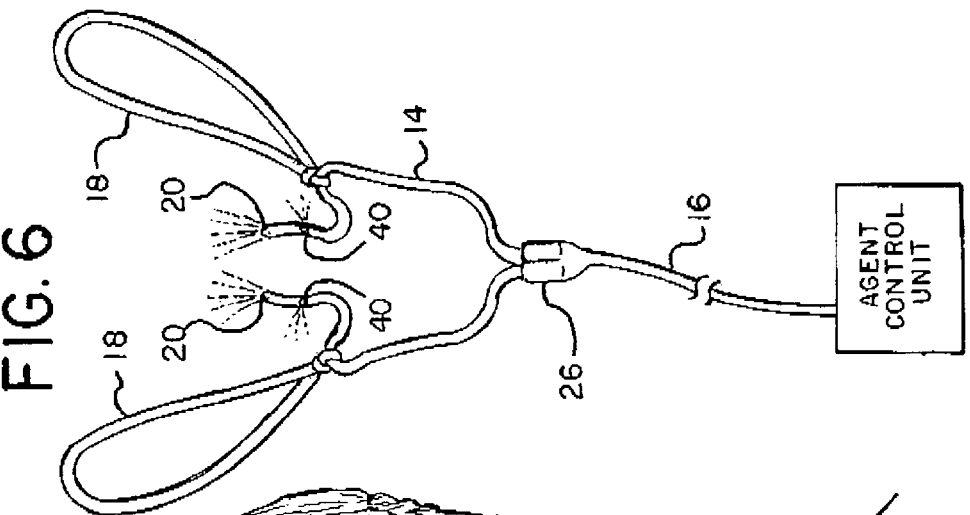
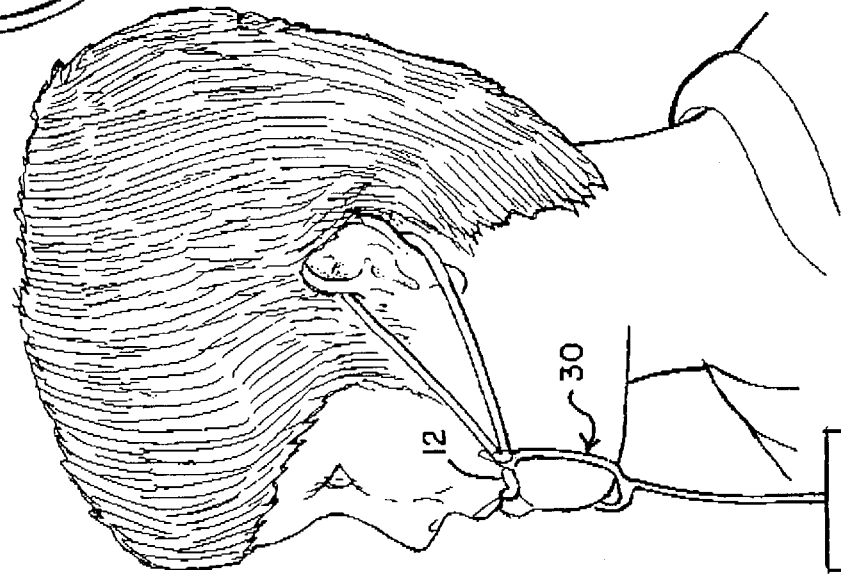
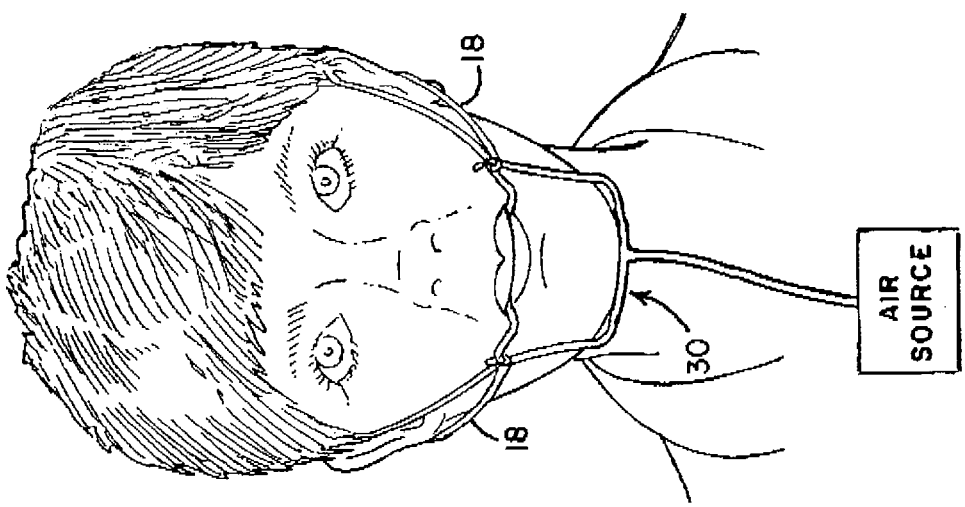

EXPERIMENTAL PROTOCOL

AIR-PULSE TRAIN DURATION VS SHAM

EFFECT OF AIR-PULSE AMPLITUDE

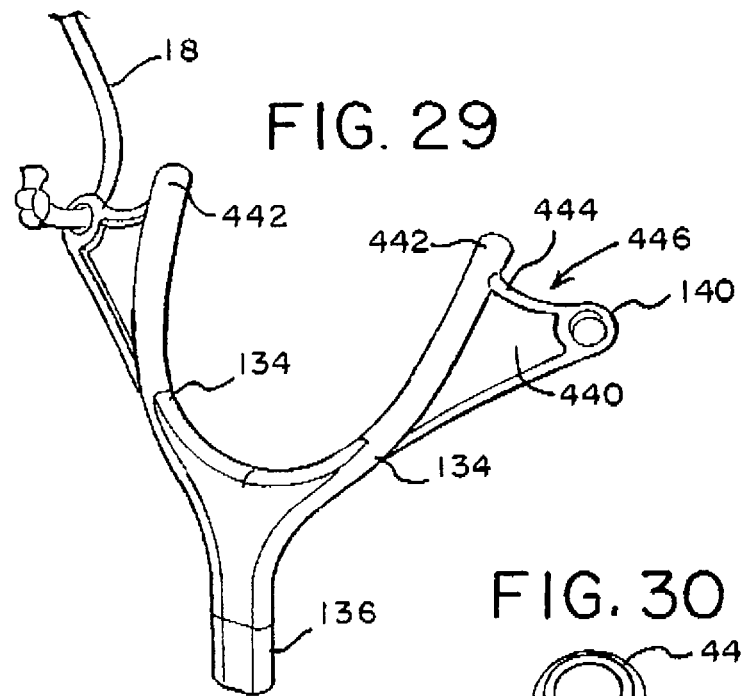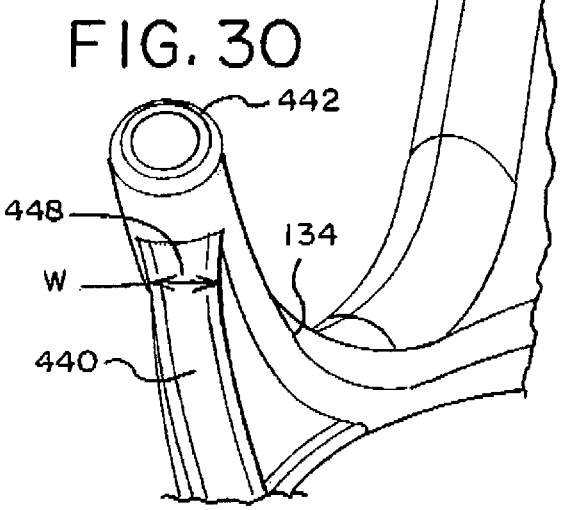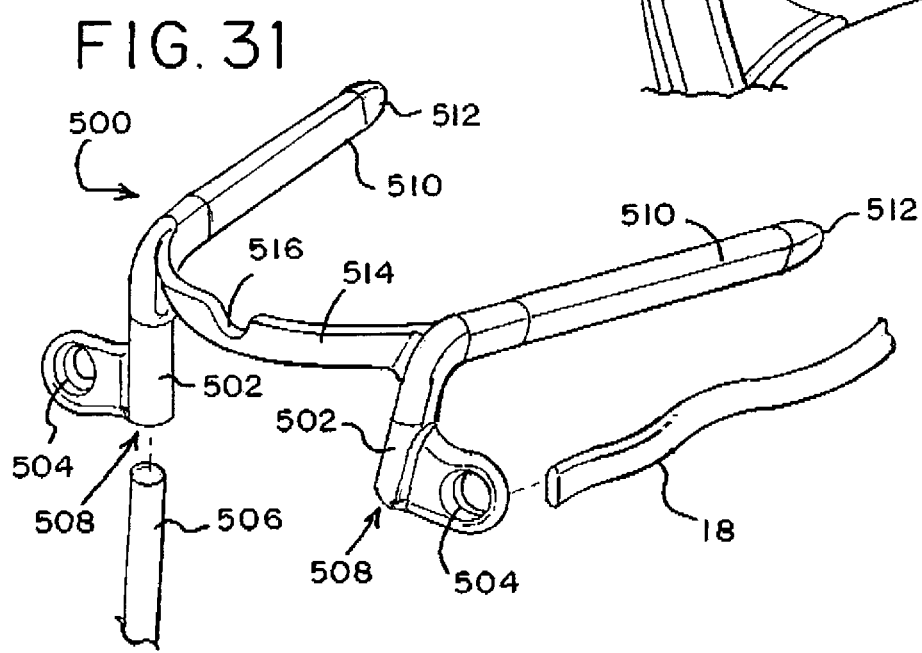

FIG. 34
FIG. 35
FIG. 36
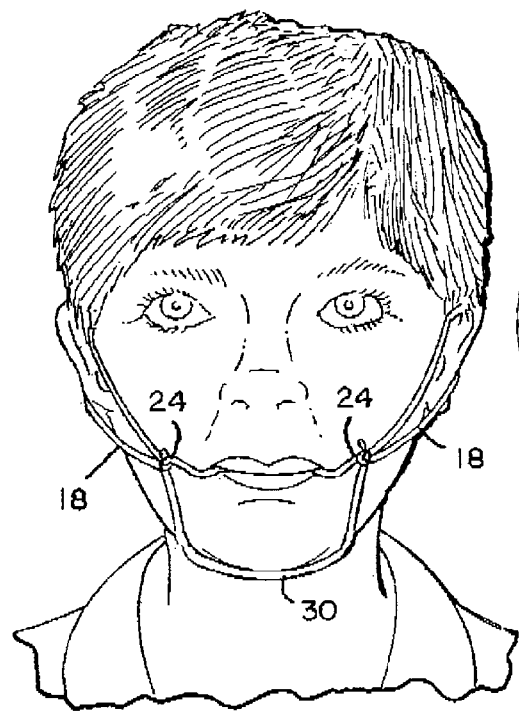
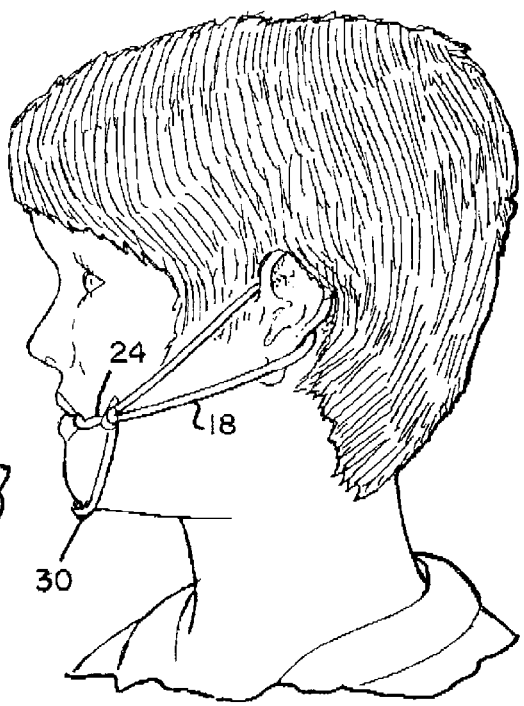
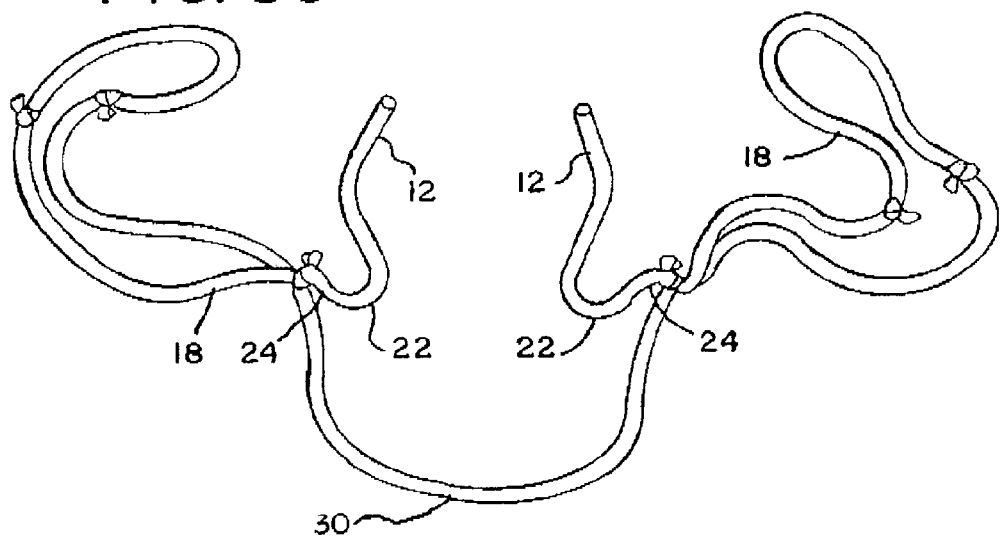

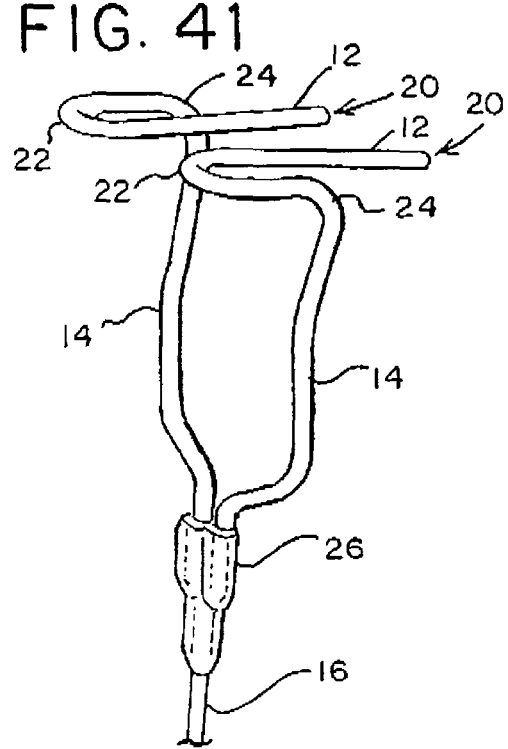
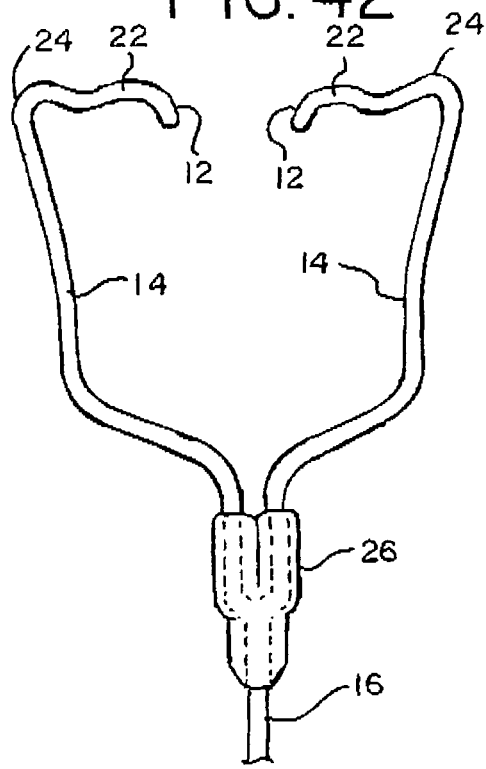
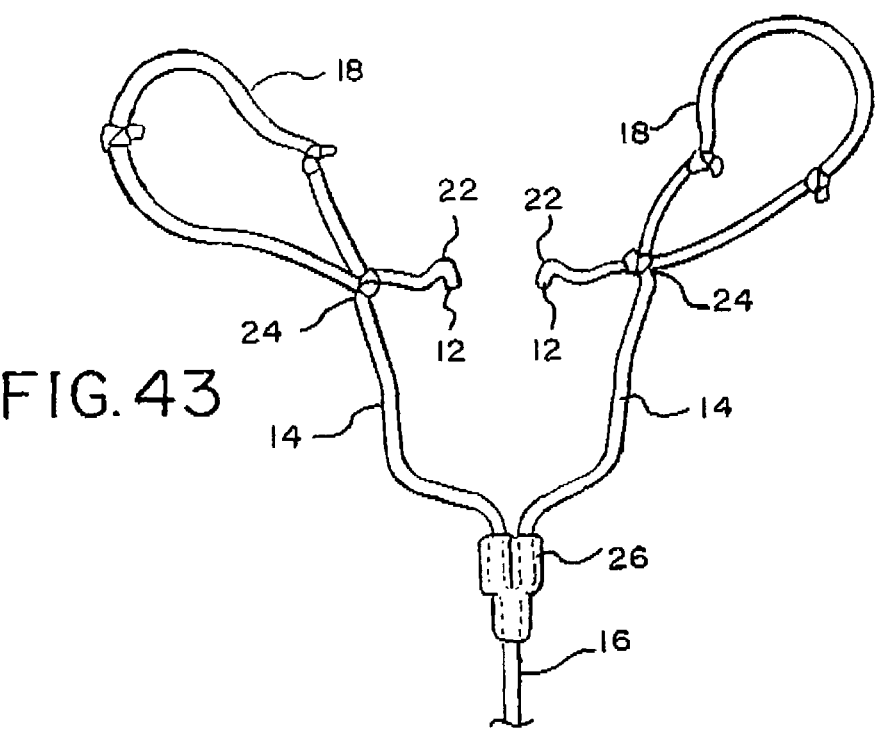

ORAL MOUTHPIECE AND METHOD FOR THE USE THEREOF

This application claims the benefit of U.S. Provisional Application No. 61/310,590, filed Mar. 4, 2010 and entitled Portable High Frequency Air Pulse Delivery Device, U.S. Provisional Application No. 61/311,145, filed Mar. 5, 2010 and entitled Oral Mouthpiece and Method for Use Thereof, and U.S. Provisional Application No. 61/417,041, filed Nov. 24, 2010 and entitled Oral Mouthpiece and Method for the Use Thereof, the entire disclosures of which are hereby incorporated herein by reference.

FIELD OF THE INVENTION

This invention relates to oral appliances and in particular a mouthpiece used to deliver at least one substance or stimulus.

BACKGROUND OF THE INVENTION

Swallowing is a complex behavior in which the output of an integrative brainstem network gives rise to a patterned movement sequence described as the pharyngeal stage of swallowing. While several lines of evidence have demonstrated the importance of oropharyngeal sensory inputs in activating this medullary swallowing network, the range of afferent patterns that are both necessary and sufficient to evoke swallowing has not been fully elucidated. Stimulation of receptive fields innervated by the superior laryngeal nerve (SLN) or the pharyngeal branch of the glossopharyngeal nerve (GPNph) appear to be particularly effective in evoking or modulating the pharyngeal swallow; these "reflexogenic" areas correspond to the laryngeal mucosa, including the epiglottis and arytenoids, the lateral pharyngeal wall, posterior tonsillar pillar and peritonsillar areas.

In humans, the anterior faucial pillar historically has been considered the most reflexogenic site for swallowing. However, the recent finding that the pharyngeal swallow may begin after the bolus head passes the anterior faucial pillars in healthy adults, including geriatric adults, suggests that stimulation of more posterior pharyngeal regions may help facilitate the initiation of swallowing. The importance of more posterior oropharyngeal areas in swallowing elicitation is also suggested by anatomic evidence that the human posterior tonsillar pillar, as well as discrete regions of the palate, pharynx and epiglottis are innervated by a dense plexus formed from the GPNph and the internal branch of the SLN. The spatial correspondence between these areas of dual SLN/GPNph innervation and reflexogenic areas for swallowing has lead to the hypothesis that swallowing is elicited most readily by stimulation of areas innervated by both the GPNph and SLN. Dynamic stimuli that excite primary afferents within a number of receptive fields over time appear to elicit swallowing more readily than do static stimuli.

A variety of stimulus modalities have been applied in attempts to evoke swallowing (for review, see Miller, 1999). Repetitive electrical stimulation of the SLN or the GPN, particularly at stimulation frequencies between 30 and 50 Hz, evokes swallowing in a number of animal species. This suggests that the repetitive nature of the stimulus, and the repetition rate, are critical variables in swallowing elicitation. More recently, electrical stimulation of the pharynx has been reported to increase both the excitability and size of the pharyngeal motor cortex representation in humans (14), and facilitate swallowing in dysphagic patients following stroke. Mechanical and chemical stimuli can evoke swallowing in animal species. In humans, reports of the effects of cold mechanical stimulation of the anterior tonsillar pillar have been variable, some authors reporting decreases in swallowing latency and increases in swallowing frequency (16), and others failing to find an effect of this type of stimulation on oropharyngeal bolus transit, esophageal coordination, or the temporal pattern of swallowing. Three studies have examined the effects of cold mechanical stimulation applied to the anterior tonsillar pillars in small samples of dysphagic stroke patients. They reported a short-term facilitation of swallowing, measured in terms of reduced delay of the pharyngeal swallow, in some patients, with no related reduction in aspiration. Longitudinal studies, examining the potential long-term effects of oropharyngeal sensitisation on not only swallowing physiology but also on nutritional and respiratory health, have not been reported. Reports on the effects of gustatory stimuli also have been variable. A sour bolus has been reported to facilitate swallowing in stroke. Whereas some authors have reported that swallowing latency is significantly reduced by a combination of mechanical, cold, and gustatory (sour) stimulation, others have reported that a cold plus sour bolus reduces the speed of swallowing.

Air-pulse trains also have been considered as a stimulus that may facilitate the pharyngeal swallow. For example, a single air pulse is a dynamic stimulus that could be applied to a number of receptive fields including regions innervated by both the GPNph and SLN. Furthermore, an air-pulse train represents a repetitive stimulus that can be applied at specific frequencies and pressures. Some devices have been suggested for delivering such air-pulse trains, as disclosed for example in US patent application 2010/0016908, the entire disclosure of which is hereby incorporated herein by reference. The air pulse trains are directed to the oral cavity by way of an oral device, which is positioned and secured through various devices. For example, the '908 publication describes, in one embodiment, an "over-the-ear" oral device configured such that the flexible tubing that delivers the air pulse trains wraps around the ears of the user.

SUMMARY

The present invention is defined by the following claims, and nothing in this section should be considered to be a limitation on those claims.

In one aspect, an oral device, or mouthpiece, is provided for delivering a stimulus, for example and without limitation a fluid, to the mouth or oropharynx of a user. In one embodiment, the oral device includes three portions: an intraoral portion, an extraoral portion, and an auxiliary support device. The auxiliary support device may include two ear loops (i.e., located on the right and left sides of the mouthpiece), or a band that surrounds the user's head, and which serve to stabilize the oral device. In one embodiment, the ear loops are knitted elastic. The intraoral portion generally includes at least one outlet port through which at least one agent or stimulus is delivered to the oral cavity or oropharynx. In one embodiment, the extraoral portion generally includes at least one (proximal) inlet port (or connector) that is connected to a control system (i.e., that generates the "agent(s)"), and at least one distal end that is continuous with the intraoral portion of the oral device.

In other embodiments, the auxiliary support device may include one or more support frames or members, including without limitation a Y-shaped yoke, a U-shaped frame, or a laterally extending support member that engages the user's face above or at an upper lip.

In other embodiments, an oral mouthpiece includes a pair of laterally spaced intraoral portions defining intraoral conduits each having at least one outlet port adapted to dispense at least one fluid pulse and an extraoral portion integrally formed with each of the intraoral portions. The extraoral portions include a pair of spaced apart lip bends communicating with the intraoral portions and a pair of chin portions extending downwardly from the lip bends, with the chin portions forming a loop positionable under the user's chin. The oral mouthpiece may be deployed with or without an auxiliary support device.

In another aspect, a method of delivering a fluid to a predetermined location in a user's mouth includes disposing a flexible tube between an outer side of a row of teeth and an inner surface of a cheek, securing the flexible tube to the user with an auxiliary support device separate from the tube and formed from a different material than the flexible tube, and dispensing the fluid through the exit port.

The various oral devices and methods for the user thereof provide various advantages. For example and without limitation, the oral device may be easily and securely positioned on the user in a reliable manner without impinging on the face of the user, and without interfering with other accessories, such as eyeglasses or hearing aids, positioned on the user.

The foregoing paragraphs have been provided by way of general introduction, and are not intended to limit the scope of the following claims. The various preferred embodiments, together with further advantages, will be best understood by reference to the following detailed description taken in conjunction with the accompanying drawings.

BRIEF DESCRIPTION OF THE DRAWINGS

The invention will now be described by way of example only, with reference to the accompanying drawings, in which:

FIG. 1 is a plan view of the oral mouthpiece of the present invention;

FIG. 2 is front view of a user with the oral mouthpiece of FIG. 1 located in an operational position;

FIG. 3 is a plan view of an alternate embodiment of the oral mouthpiece of the present invention;

FIG. 4 is a front view of a user with the oral mouthpiece of FIG. 3 located in an operational position;

FIG. 5 is a side view of the user of FIG. 4;

FIG. 6 is a plan view of an alternate embodiment of the oral mouthpiece of the present invention similar to that shown in FIG. 1 but showing a plurality of ports;

FIG. 29 is a perspective view of an alternative embodiment of a yoke.

FIG. 30 is a partial end view of one side of the yoke shown in FIG. 29.

FIG. 31 is a perspective view of an alternative embodiment oral device.

FIG. 34 is a front view of the oral mouthpiece shown in FIG. 32 applied to a user.

FIG. 35 is a side view of the oral mouthpiece shown in FIG. 32 applied to a user.

FIG. 36 is an alternative to view of the oral mouthpiece shown in FIG. 33.

FIG. 41 is a side view of the oral mouthpiece shown in FIG. 1 without an auxiliary support device secured thereto.

FIG. 42 is a front view of the oral mouthpiece shown in FIG. 41.

FIG. 43 is a front view of the oral mouthpiece shown in FIG. 42 with an auxiliary support device secured thereto.

DETAILED DESCRIPTION OF THE DRAWINGS

Figure 7:
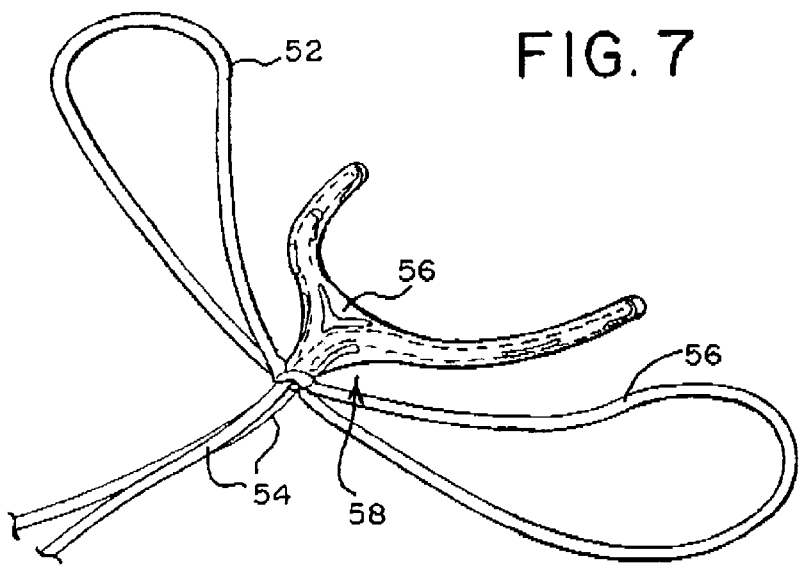
FIG. 7 is a perspective view of another embodiment of the oral mouthpiece of the present invention.

Referring to FIGS. 1, 2 and 39-43, one embodiment of an oral mouthpiece is shown generally at 10. The oral mouthpiece 10 includes intraoral portions 12, extraoral portions 14 and an auxiliary support device, configured in this embodiment as ear connectors 18. The extraoral portions 14 include a supply portion 16. The intraoral portions 12 define intraoral conduits. The extraoral portions 14 define an extraoral conduit. The intraoral conduit is in flow communication with the extraoral conduit.

The intraoral portion 12 of the mouthpiece 10 enters the mouth at the angle or corner of the mouth on the user's right and left sides. The intraoral portion 12 extends along the buccal cavity, or vestibule, lateral to the teeth and medial to the cheek, on the right and left sides of the mouth. The length of the intraoral aspect is typically between 20 mm and 50 mm for human adult users, and may be less for pediatric users. The lengths of the intraoral portions may be modified by the user by advancing, or retracting, the intraoral segment that is in flow communication with the extraoral segment, relative to the auxiliary support device. This is an advantage of the device in that the intraoral segments may be modified to accommodate the user's specific oral anatomy. The intraoral portion or aspect 12 ends caudally with an output port 20 such that an agent or substance or stimulus can be delivered from this output port 20 in the general region of the posterior mouth or oropharynx on the right and left sides.

In one embodiment, the intraoral portion 12 is oriented superiorly and caudally within the buccal cavity such that the output port 20 is situated lateral to the maxillary premolars or molars during use. One advantage of having the intraoral portion or aspect 12 angled superiorly from its origin at the corner of the mouth is that the output port 20 of the mouthpiece does not come in contact with pooled saliva that may accumulate in the region of the mandibular dental arch. However, the intraoral portion 12 of the mouthpiece may be oriented along a variety of angles, relative to the horizontal plane, providing a means for positioning the output port 20 lateral to the mandibular molars, or along the occlusal plane, depending upon the specific conditions and requirements of the user including the oral anatomy and the dentition.

In another aspect, the intraoral portion 12 of the mouthpiece 10 may be oriented along a variety of angles, relative to the user's sagittal plane, and be gently curved, along this principal off-sagittal orientation, such that it follows the natural contour of the buccal cavity and maxillary or mandibular dental arches, thereby providing optimal comfort for the user. The general orientation and local curvature of the intraoral portion 12 can be provided as manufactured aspects of the mouthpiece 10. Alternatively, the mouthpiece can be provided such that these aspects of the intraoral portion 12 can be manually molded by the clinician, caregiver, or user. The capacity to orient and curve the intraoral aspect of the mouthpiece can be provided by a length of fine malleable wire being embedded within the intraoral portion 12 of the mouthpiece on the left and right sides of the mouth. This may represent an advantage in that the user, or caregiver, would be provided a means of molding the mouthpiece to the specific anatomy of the individual user.

In another aspect, the intraoral 12 and extraoral 14 portions of the mouthpiece are continuous as right and left or pair of first looped regions 22 of mouthpiece that are positioned at the right and left angles or corners of the user's mouth during use. These two looped regions, which form lip bends, are oriented approximately in parallel with the user's axial or horizontal plane, at the level of the angles of the mouth.

The looped regions 22 where the intraoral 12 and extraoral 14 portions of the mouthpiece meet at the angles of the mouth are contiguous with a second, extraoral looped or curved region 24 that provides a site of attachment or site of origin for an auxiliary support device. In other embodiments, the looped region 24 may be omitted. In one embodiment, the auxiliary support device is configured as ear connectors 18 that are attached on the right and left sides of the mouthpiece 10. The ear connectors 18 may be ear loops that are made of a different material than the intraoral or extraoral portions. In one embodiment, the ear loops are knitted elastic ear loops. The second looped region 24 is oriented at approximately 45 degrees relative to the sagittal plane of the user on the right and left sides of the mouthpiece. In use the second looped regions 24 sit over the face, immediately lateral to the angle of the mouth on the right and left sides, and does not extend rearwardly and/or upwardly for connection to the ears of the user. Rather, these looped regions 24 provide a point of origin for the auxiliary support device, such as the around-the-ear soft elastic ear loops 18 on the right and left sides of the mouthpiece. By virtue of their orientation relative to the intraoral portions, these ear loop origin sites and associated ear loops provide a means of stabilizing the intraoral segments 12, without the elastic tending to pull the intraoral segment 12 out of the mouth. These looped regions 22 and 24 are continuous with a communicating region that extends inferiorly from the inferior aspect of the second looped portion for approximately 30 mm to 100 mm and then curves medially toward the user's midline plane so as to form a chin loop. As the right and left portions of the mouthpiece approach the midline, they articulate with a Y-connector 26, providing a means of delivering an agent from a single input post to right and left intraoral aspects of the mouthpiece.

Figure 44:
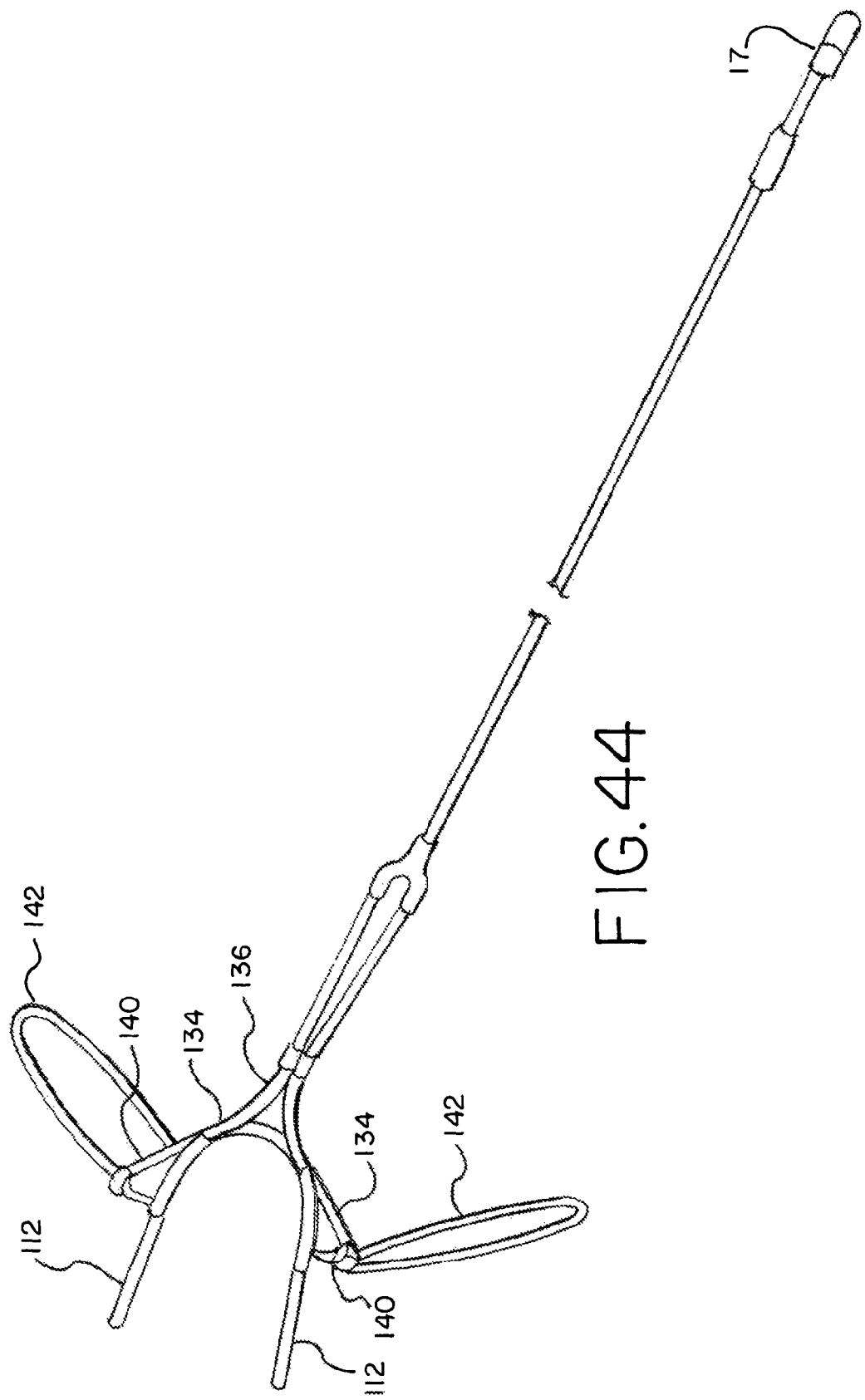
FIG. 44 is a perspective view of one embodiment of an oral mouthpiece.

In one embodiment, the Y-connector 26 is connected to the supply portion 16 of the mouthpiece 10, which supply portion continues for approximately 90 cm. The length of the supply portion 16 may extend from 0.50 meters to about 2.0 meters as shown in FIG. 44. A longer supply portion 16 is an advantage in that the mouthpiece user may move fairly freely in relation to the fluid control unit. For example, the mouthpiece use could move between lying and sitting in a hospital bed with the fluid control unit mounted on the head or side rail of the bed. This feature increases the clinical utility of the mouthpiece system in the health care and home settings. At the end of the supply portion tube, a male luer connector may be provided. Alternatively, a low pressure one-way check valve luer connector 17 is provided. This is to prevent contamination of the control unit by any fluids, bodily or otherwise, that may traverse the tubing 16. The check valve 17 may reduce the flow into the mouthpiece, dropping the flow rate to 2.4 to 2.5 L/min. The flow may be maintained above 2.0 L/min. The frequency and amplitude are not affected by the inclusion of the check valve 17.

A control unit 28 is connected to the distal end of the supply portion 16 of the mouthpiece 10. The control unit 28 generates at least one agent, or delivers at least one agent to the supply portion 16 of the mouthpiece 10. Preferably the Y-connector is adjustable so that it can extend past the cheek/jaw thereby minimizing a patient's tendency to dislodge the mouthpiece. However, there may be instances when a longer portion 14 is desirable, for example, in patients who are very sensitive to contact about the face and mouth.

Figure 32:
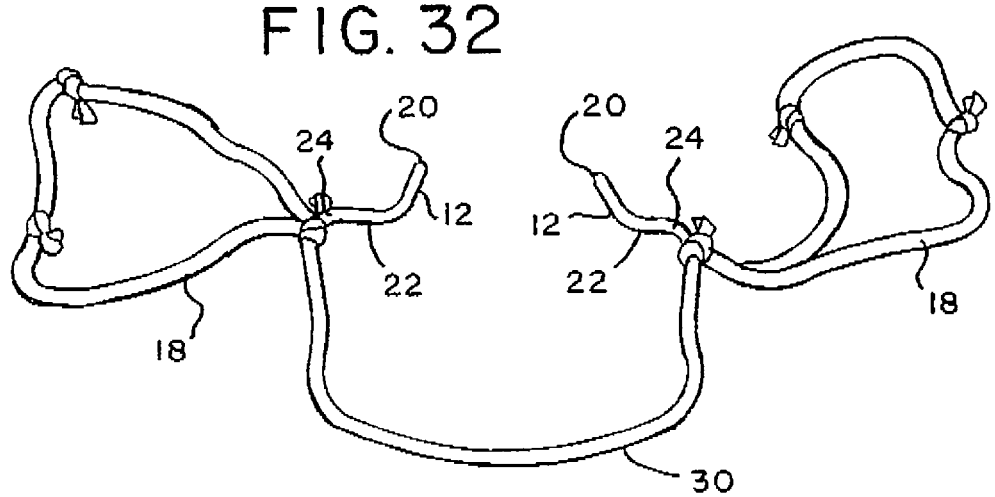
FIG. 32 is a front, perspective view of the oral mouthpiece shown in FIG. 3.
Figure 33:
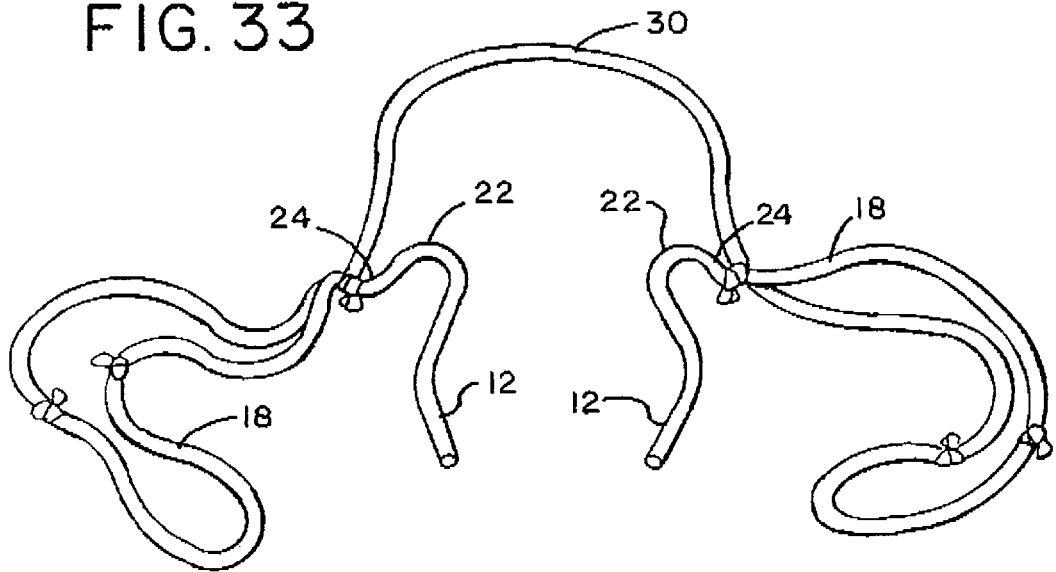
FIG. 33 is a top view o the oral mouthpiece shown in FIG. 32.

In another embodiment shown in FIGS. 3-5 and 32-36, a continuous chin loop or region 30 is provided, extending from the right elastic attachment loop 24 (shown in FIGS. 3 to 5) and, running inferiorly to the level of the user's chin, crossing the midline immediately anterior to the chin, and extending to the other side of the face where it runs superiorly and continues as the left elastic attachment loop 24 as best seen in FIGS. 4 and 32.

In another aspect, one embodiment of the auxiliary support device is configured as ear loops 18 attached to the second looped 24 aspect of the extraoral portion 14 of the mouthpiece 10, described above. In one embodiment, the ear loops 18 are made of knitted nylon polyester elastic and are between 4 cm and 25 cm in length and between 1 mm and 7 mm in width. The ear loops 18 originate from a single site on the second curved portion 24 of the mouthpiece 10. There are several advantages afforded by the ear loops 24. In one embodiment, the auxiliary support device, and in particular the ear loops or head band, are more compliant or flexible (less stiff) than the extraoral and/or intraoral portions. For example, the ear loops or head band may have a much lower modulus of elasticity than the intraoral and extraoral portions, made for example of thermoformed tubing. The ear loops or head band provide a means of stablilizing the mouthpiece during use. Being made of soft, knitted elastic material such as nylon polyester, the ear loops stretch substantially such that the mouthpiece can be effectively and comfortably stabilized and worn by individuals with different cranial and facial anatomy. The soft knitted material reduces the likelihood that the mouthpiece will cause discomfort or tissue damage to the hairy skin of the face or pinna. The narrow width and malleability/flexibility of the knitted elastic ear loops is another advantage in that the ear loops do not interfere with over-the-ear hearing aids or the over-the-ear portion of eyeglasses. This is particularly important since users of the mouthpiece will include older adults, as well as pediatric users who require eyeglasses and hearing aids as the result of congenital syndromes or conditions. The soft, knitted ear loops provide user comfort, even when the mouthpiece is used for extended periods of time.

In use, some flexibility at points 20, 22, and 24 provide a means of improving the fit, efficacy, and comfort of the mouthpiece for faces of various shapes and sizes. Some degree of malleability in the chin piece 30 (shown in FIGS. 3 to 5) and extraoral portions 14 (shown in FIGS. 1 and 2) is also advantageous in that this allows improved positioning of the two sections that rise up toward the angles of the mouth.

Another advantage of the knitted ear loops 18 is that many users, caregivers, and clinicians are familiar with them based on previous experience with ear loops on medical masks. Thus, the ear loops 18 will facilitate easy positioning of the mouthpiece by users by virtue of their general familiarity with the procedures around knitted ear loops. Even for users who have not previously used knitted ear loops, there is an intuitive element around ear loops that would increase the likelihood that a naive user would position them correctly around the ears.

The mouthpiece 10 may be made of flexible tubing, for example, a pair of flexible tubes configured to be positioned on opposite sides of the face of a user. The oral device may include only a single tube positioned on one side of the user's face, for example, for the purpose of delivering an agent to one side of the mouth or oropharynx. This may be advantageous, for example, in patients who have undergone unilateral surgery for oral cancer, or in the case of a unilateral sensorimotor impairment of the face, mouth, or oropharynx.

The flexible tubes may be made of tubing which can be shaped into a given configuration but which has some flexibility and ability to conform to the face and mouth of the user. The tubes may have a ⅛th inch outer diameter and a 1/16th inner diameter forming a lumen. In various embodiments, the intraoral and/or extraoral portions may be made of various materials, including without limitation, polyurethane, polyethylene, PVC, silicone, rubber, or other suitable and biocompatible materials, and/or combinations thereof. In one embodiment, the tubing is 1.6 mm ID×3.2 mm OD tubing made of TYGON® MPF-100 available from Saint-Gobain, Akron, Ohio.

It will be appreciated by those skilled in the art that the intraoral portions 12 may have a plurality of ports 40 formed therein in addition to the ports 20 positioned at the distal end of the intraoral portions 12.

Figure 37:
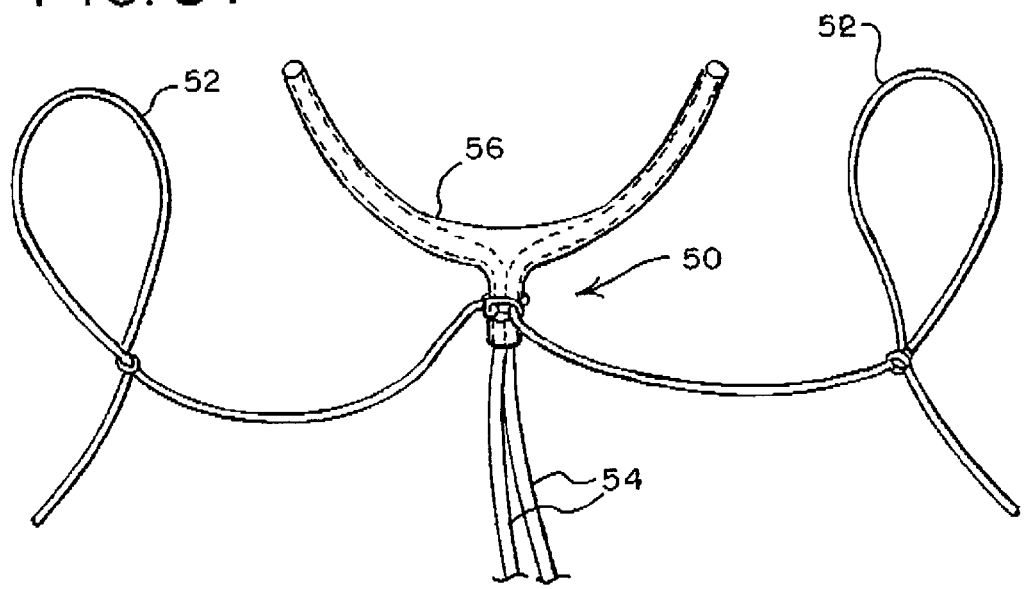
FIG. 37 is a top view of the oral mouthpiece shown in FIG. 7.
Figure 38:
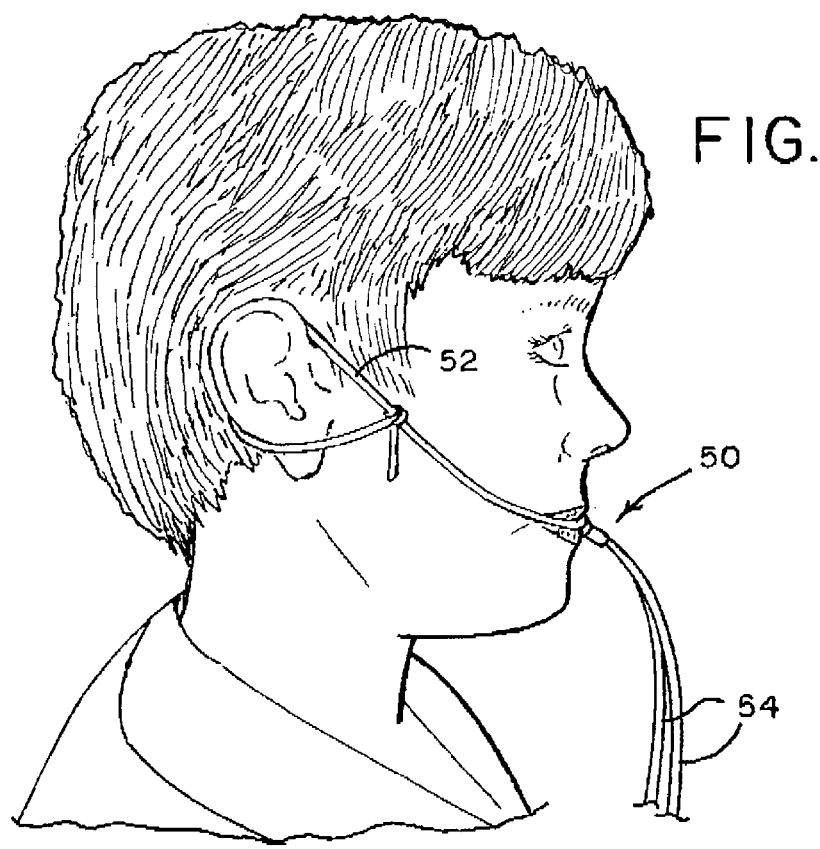
FIG. 38 is a side view of the oral mouthpiece shown in FIG. 37 as applied to as user.
Figure 39:
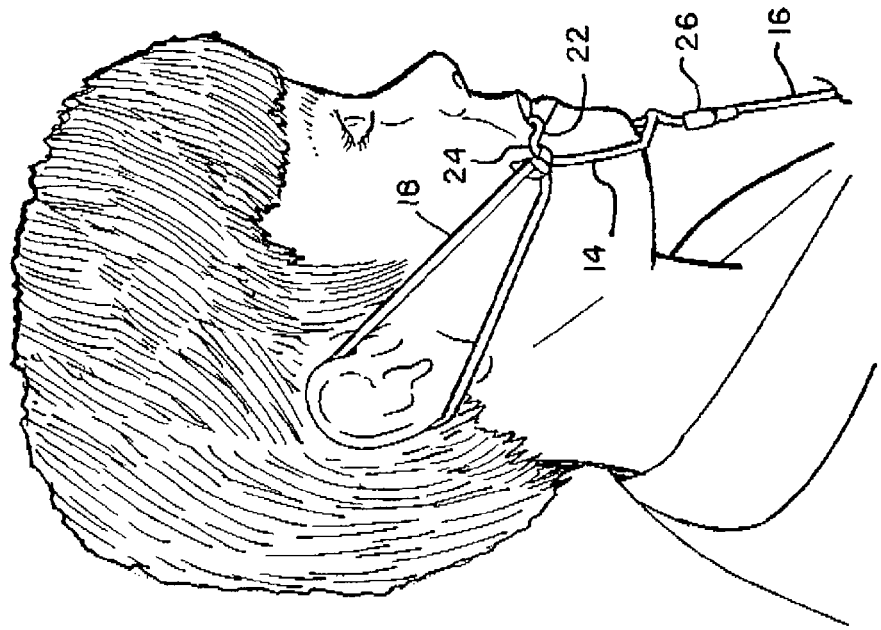
FIG. 39 is a front view of the oral mouthpiece shown in FIG. 1 as applied to a user.
Figure 40:
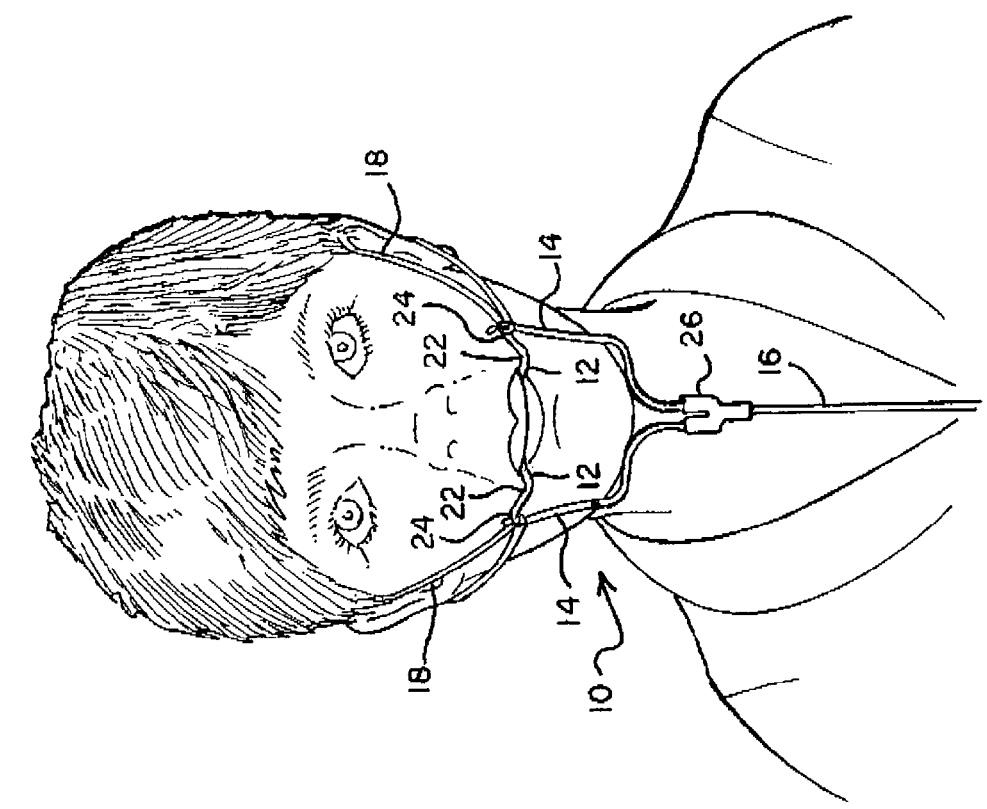
FIG. 40 is a side view of the oral mouthpiece shown in FIG. 29 as applied to a user.

Referring to FIGS. 7, 37 and 38, the oral device 50 shown herein and fully described in US 2010/0016908 and WO 2009/127947, both of which are hereby incorporated herein by reference, may be improved upon by adding an auxiliary support device, shown as ear loops 52. Ear loops 52 are similar to those described above but are attached to the extraoral portion 54 proximate to where the extraoral portion 54 meets the intraoral portion 56. While the ear loops 52 serve to secure the oral device 50 to a user in a secure fashion. In the absence of earloops, this embodiment has the shortcoming that it can move out of position when the subject opens his/her mouth, or in patients with mouth/lip weakness the mouthpiece 50 could move out of position during use.

Figure 23:
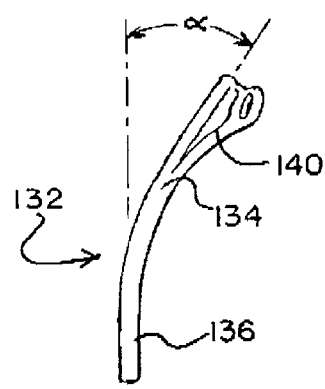
FIG. 23 is a side view of the yoke shown in FIG. 20.
Figure 22:
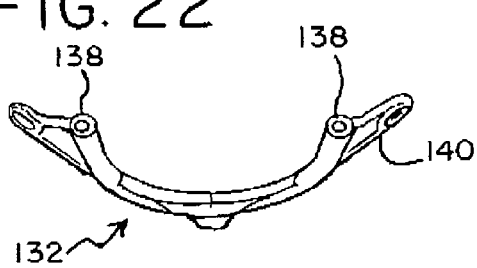
FIG. 22 is a top, perspective of the yoke shown in FIG. 20.
Figure 20:
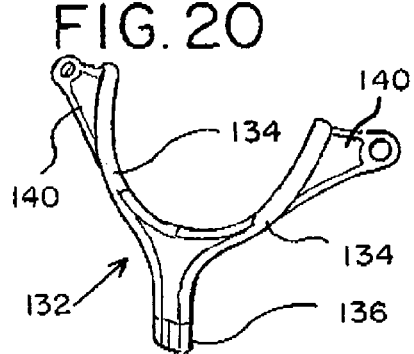
FIG. 20 is a perspective view of the yoke shown in FIG. 19.

Referring to FIGS. 19-23, 29-30 and 44, another embodiment of an oral device is shown. The oral device includes a pair of laterally spaced intraoral portions 112 defining intraoral conduits each having at least one outlet port 120 adapted to dispense at least one fluid pulse. An extraoral portion 114 is integrally formed with each of the intraoral portions. The extraoral portions define extraoral conduits in flow communication with the intraoral conduits. An auxiliary support device includes a yoke. In one embodiment, the yoke is configured as a Y-shaped frame 132 having a pair of arm portions 134 and an inlet portion 136, each configured with grooves or channels in which the extraoral portions are disposed and secured. As shown in FIG. 23, the arm portions curve rearwardly from the inlet portion. In one embodiment, the arm portions extend at an angle α of about 20-60 degrees, and in one embodiment at an angle α of about 30-45 degrees, and in one embodiment at an angle α of 38.5 degrees. The frame shapes and holds the extraoral portions. In addition, each of the pair of arm portions 134 includes a wing with an attachment member 140. At least one securing member 142, configured for example and without limitation as an elastic band, may be secured to the attachment members 140. The band may be configured as a pair of ear loops, or as a single headband that encircles the user's head and locates and holds the yoke in position.

Referring to FIGS. 29 and 30, in one embodiment, wing portions 440 have a concave curved portion 444 that interfaces with the lips, or corner of the user's mouth, with the end portions 442 of the yoke arms extending into, and positioning intraoral portions of the tubing, in the mouth of the user. In essence, the end portions 442 and the attachment member 140 have a recess 446 formed therebetween so as to locate the yoke relative to the user, and the lips/mouth in particular, with the force applied by the securing member 18 urging the yoke against the user's lips/mouth. Referring to FIG. 30, the width (W) of the wing 440 may be widened at the junction 448 of the end portions 442 and the wings 440 at the area of contact with the user's lips/mouth so as to reduce the tissue contact pressure.

Figure 24:
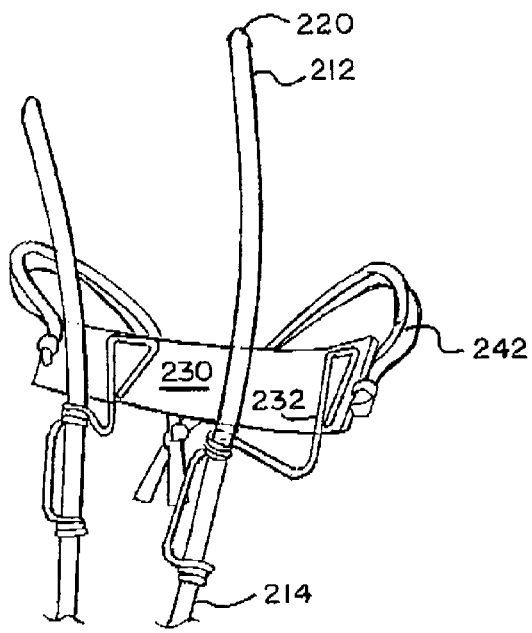
FIG. 24 is a partial, perspective view of an alternative embodiment oral device.
Figure 25:
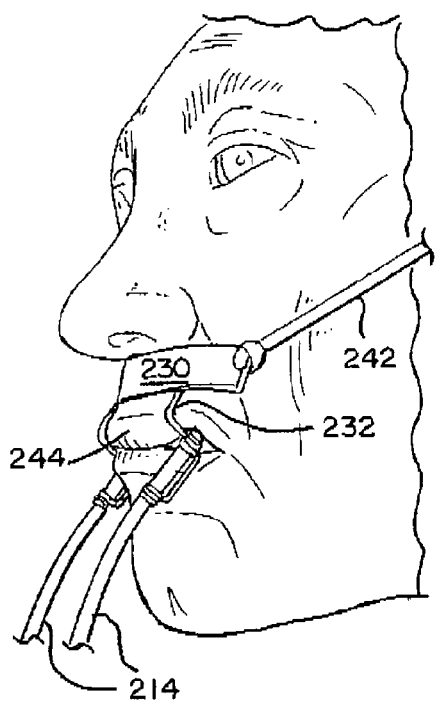
FIG. 25 is a side view of the oral device shown in FIG. 24 applied to a user.
Figure 26:
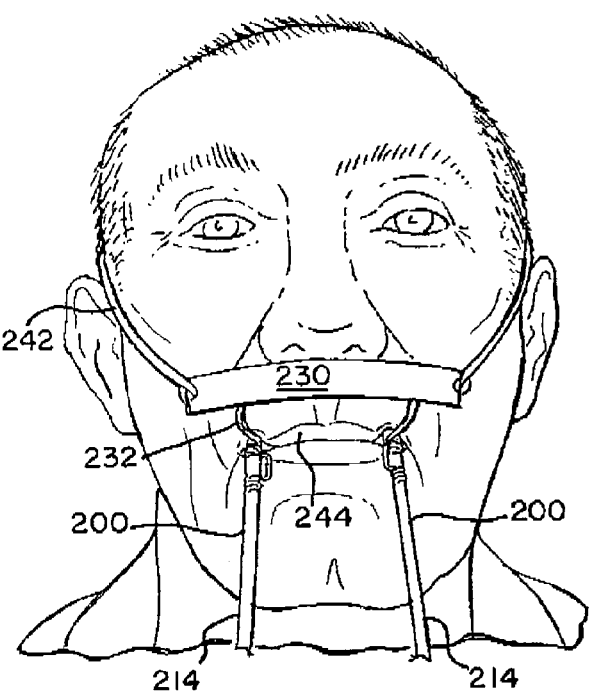
FIG. 26 is a front view of the oral device shown in FIG. 24 applied to a user.

Referring to FIGS. 24-26, another embodiment of the oral device includes a pair of tubes 200, each defining intraoral and extraoral portions, and which may be configured as substantially straight, flexible tubes, or may include lip bends as described above. A laterally extending support member 230 extends transversely to the tubes 200 and is positioned above an extraoral portion 214. The support member 230 may engage the user's face above or on/at an upper lip thereof. The support member 230 may be made of a cloth-like material, and may be elastic or non-elastic. The support member is coupled to the tubes 200 with a pair of clips 232. The clips 232 may be wrapped around the tubes, and are secured to the support member with fasteners, adhesives or combinations thereof. The clips 232 may include a lip bend portion that wraps around the upper lip of the user. At least one securing member 242 is coupled to opposite ends of the support member. The securing member may be configured as a pair of ear loops, or as a single head band. In use, the intraoral portions 212 are disposed in the user's mouth, with the support member 230 supported by the user's upper lip and securely held thereto with the securing member 242. This device may be particularly well suited for individuals that may have particular ailments or sensitivities around and under the chin.

Figure 27:
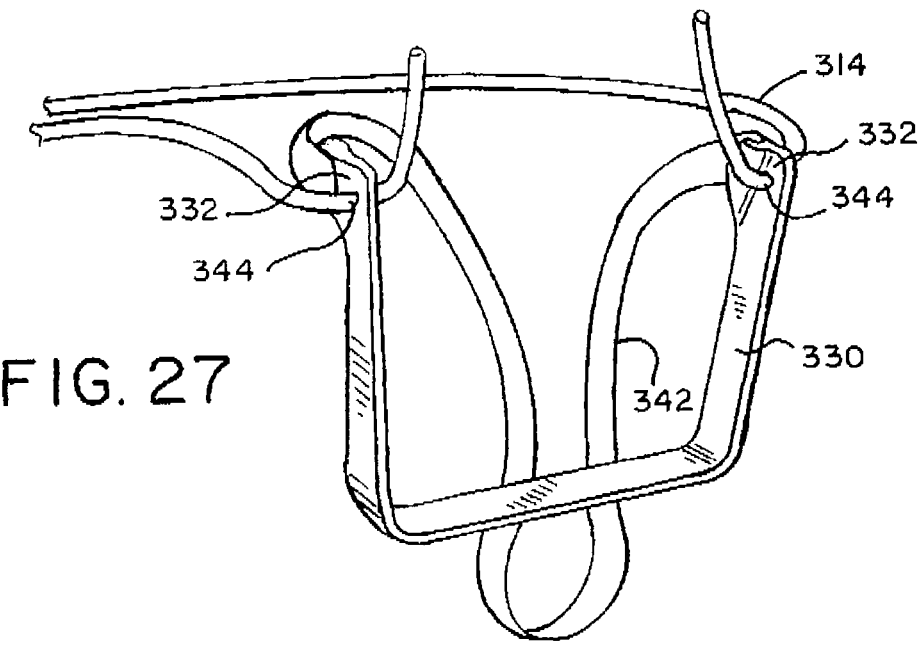
FIG. 27 is a partial, perspective view of an alternative embodiment oral device.
Figure 28:
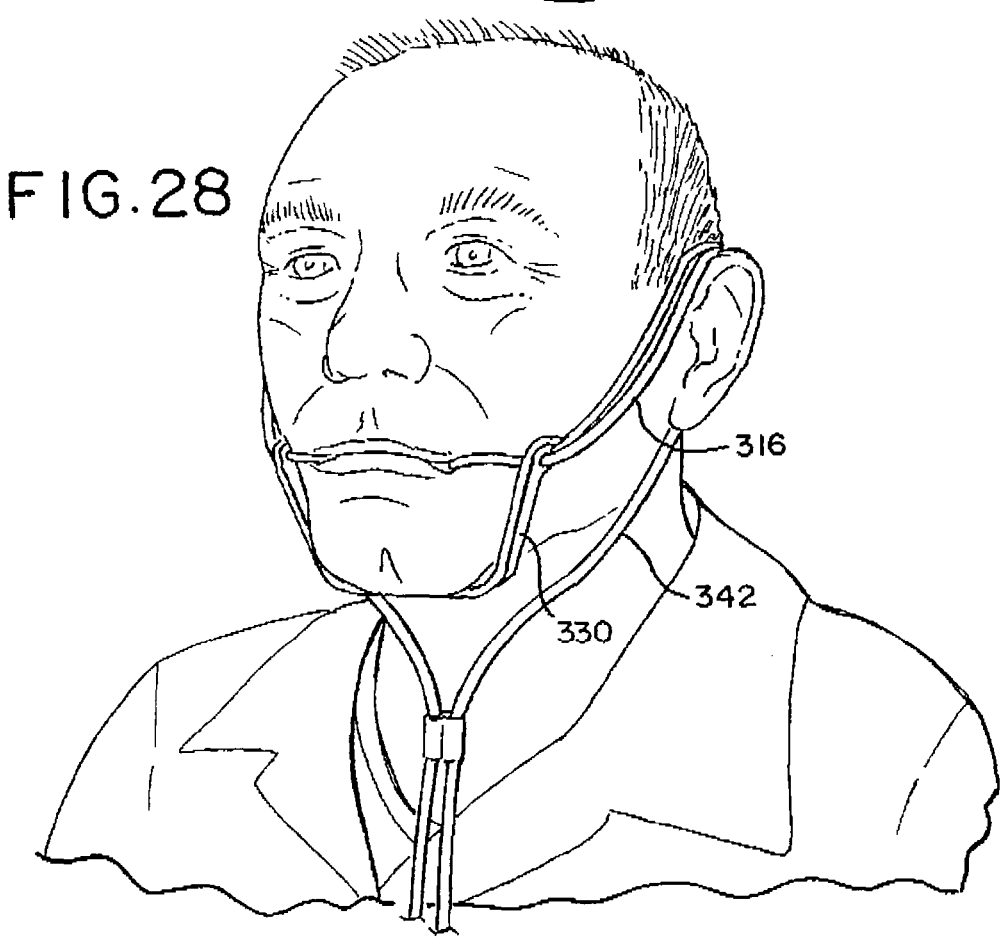
FIG. 28 is a perspective view of the oral device shown in FIG. 27 applied to a user.

Referring to FIGS. 27 and 28, another embodiment of an auxiliary support device includes a U-shaped frame 330 shaped and configured to be positioned under the user's chin. The frame has opposite end portions 332 coupled to an extraoral portion 314, and at least one securing member 342 coupled to the opposite end portions 332. For example, the tubes making up the extraoral portions may extend through openings 344 formed in the end portions. The U-shaped frame may be made from a flexible, but semi-rigid material, such as a plastic strip. The extraoral portions 314 may include ear loop portions 316, thereby forming an integral securing member, or may extend downwardly along the chin as shown for example in the embodiment of FIG. 1. At least one securing member 342, configured as individual ear loops or as a head band may be additionally secured to the end portions, or may be the sole support for the end portions. The securing member locates and holds the support device firmly in position.

Referring to FIG. 31, another embodiment of an oral device 500 includes a pair of downwardly extending extraoral inlet portions 502, each configured with an attachment member 504, or loop, that may be coupled to a securing member, such as an ear loop or head band. The inlet portions have an opening 508 shaped and dimensioned to receive an auxiliary extraoral tube 506. The oral device further includes integrally formed intraoral portions 510, which are shaped and contoured to be positioned in the vestibule of the user's mouth between the teeth and inner cheek/lips. The intraoral portions are in fluid communication with the extraoral inlet portions, and thereby with the tubes 506 positioned in the inlet portions. The ends of the intraoral portions are each configured with a fluid exit port 512. An intraoral bridge 514 extends between the opposing pairs of inlet portions/intraoral portions. The bridge 514 is curved and shaped/dimensioned to be positioned in the vestibule. A cutout 516, or clearance opening, is formed in a mid/intermediate portion of the bridge to provide clearance for the maxillary labial frenulum. In one embodiment, the intraoral portions and bridge 510, 514 are positioned between the upper teeth and the user's cheek, with the inlet portions 502 extending downwardly. In another embodiment, the intraoral portions are positioned between the lower teeth and cheeks, with the inlet portions extending upwardly. A securing member 18, e.g., ear loops or head band, is coupled to the attachment members and secures the oral device to the user. The oral device may be made of a molded rubber compound, or of various polymers otherwise herein described.

In any of the embodiments, a wire may run along a length of at least a portion of the flexible tubing forming either or both of the intraoral and extraoral portions. The wire provides further shape memory to the flexible tubing. For example, the oral devices disclosed herein may be shaped by inserting a length of fine wire into the tubing and then bending the wire.

There are a number of advantages realized with the different embodiments of the oral mouthpiece of the present invention. Specifically the mouthpiece is stabilized during use by the user by the auxiliary support devices, including for example and without limitation the soft elastic loops that fit around the ears. This advantage provides a means of maintaining the intraoral aspects of the mouthpiece in appropriate position, even when the lips are open (as in the case of a patient with lip weakness), during talking, and during other behaviours such as yawning, eating, chewing, and drinking from a glass or straw. Importantly, this feature of the mouthpiece prevents the intraoral portions of the mouthpiece from migrating toward the pharynx, or in other directions, during use by a person, thus enhancing the safety aspect of the device.

Use of the auxiliary support devices stabilizes the mouthpiece so as to reduce the likelihood that the stabilization component of the mouthpiece will be perceived as irritating by the user and cause tissue damage with prolonged use.

The head band and soft, elastic ear loops are intuitive in terms of positioning, since they are used in other devices with which the user has likely had previous experience, for example, a medical face mask. The head band and soft elastic ear loops are straightforward to manipulate, thereby facilitating correct positioning by patients. The elastic bands are also narrow, occupying very little area over and around the pinna of the ear or rear of the skull, thus allowing easy positioning and use by persons who wear glasses or over-the-ear hearing aids.

In the various embodiments, there is no mouthpiece material occupying the midline region of the mouth. Rather, the intraoral portions of the mouthpiece enter the mouth as the angles of the mouth on the left and right sides, leaving the midline oral region free to engage in talking, eating, drinking, and other oral behaviours, and providing a situation in which the appearance of the mouthpiece is considered more socially appropriate than with devices that occupy the midline oral region. Of course, it should be understood that the conduit may extend along the midline of the chin, and then diverge to the left and right sides of the mouth.

The tubing comprising the mouthpiece is molded such that the left and right intraoral portions extend outside the mouth at the angles as an extraoral portion that is continuous between the right and left sides, and that extends inferiorly to run laterally at the level of the chin. An important advantage of this aspect of the mouthpiece is that it prevents the mouthpiece from being swallowed. In one embodiment, this extraoral portion of the mouthpiece can be used to further tether the mouthpiece, or to attach other devices.

The mouthpiece is relatively small and light-weight. In one preferred embodiment, it is envisaged that the mouthpiece can be readily manufactured at minimal cost, given the simplicity of the design, the small length of tubing required, and the low costs of the other required materials such as the elastic.

The mouthpiece can be easily connected to the output of an air-pressure regulator through a length of tubing that extends from the extraoral portion of the mouthpiece in the region of the mandible.

The mouthpiece comes manufactured with a looped configuration, oriented on the horizontal plane that fits around the angle of the mouth. This aspect of the tubing is contiguous with a second loop that is situated extraorally, immediately lateral to the angle of the mouth and oriented approximately 45 degrees relative to the user's midsagittal plane. The soft elastic ear loops originate at this second looped region and extend over and around the pinna of the ears. With this design, the elastic ear loops do no pull directly on the intraoral portions of the mouthpiece, causing them to migrate. Rather, the elastic ear loops pull on the second looped area (described above) with the result that the intraoral portions of the mouthpiece remain stable during use.

The mouthpiece can provide an attachment platform for other oral device(s), or oral device components.

The mouthpiece can be used as an oral suction catheter.

The intraoral portions of the mouthpiece can be provided as colored elements, providing a cue to the user regarding the portion of the device that is to be inserted into the mouth; by coloring the two intraoral and/or extraoral segments different colors, and providing associated written instructions (e.g., green=right, red=left), the mouthpiece provides increased assurance that the mouthpiece will be positioned accurately and not positioned upside down. "Right" and "left" icons can also be provided, as well as "finger icons" showing the positions where the fingers should be placed during placement.

The user can close the lips while the mouthpiece is in position, allowing the user to maintain a typical facial rest position during use.

Importantly, there is no mouthpiece material disposed between the contacting surfaces of the upper and lower teeth. This is advantageous since a significant distance between the upper and lower teeth may reduce the user's ability to swallow with the device in position.

There is no material between the superior surface of the tongue, and the palate. This is also an advantage in terms of swallowing since swallowing requires approximation of the superior tongue surface and the palate to transport ingested material from the mouth to the pharynx.

The mouthpiece can be provided with a flavored element within the intraoral portion, on the surface of the intraoral portion, or on or within the extraoral portion that runs outwardly between the user's upper and lower lips. This flavoring may increase the acceptability of the mouthpiece, as well as promote salivary flow, and swallowing.

The mouthpiece is small and portable. It can be fit into a purse or small carrying bag, or into a typical "sandwich baggie" for easy and clean transport.

The agent(s) delivered to the mouth and oropharynx via the mouthpiece described herein may include, but are not limited to, a fluid, including a gas or liquid. For example, air may be delivered to the posterior oral cavity and oropharynx via the mouthpiece. In this regard, our previous studies, as well as those from other laboratories, have shown that application of air-pulse trains to the oropharynx increases saliva swallowing rates in young and older adults, and activates regions of the human cerebral cortex. Tests were undertaken to determine the effects of oropharyngeal air-pulse: train duration, amplitude, and frequency on saliva swallowing rates in dysphagic stroke and to determine saliva swallowing rates associated with air-pulse application different from swallowing rates associated with a sham condition, in dysphagic stroke.

Figure 8:
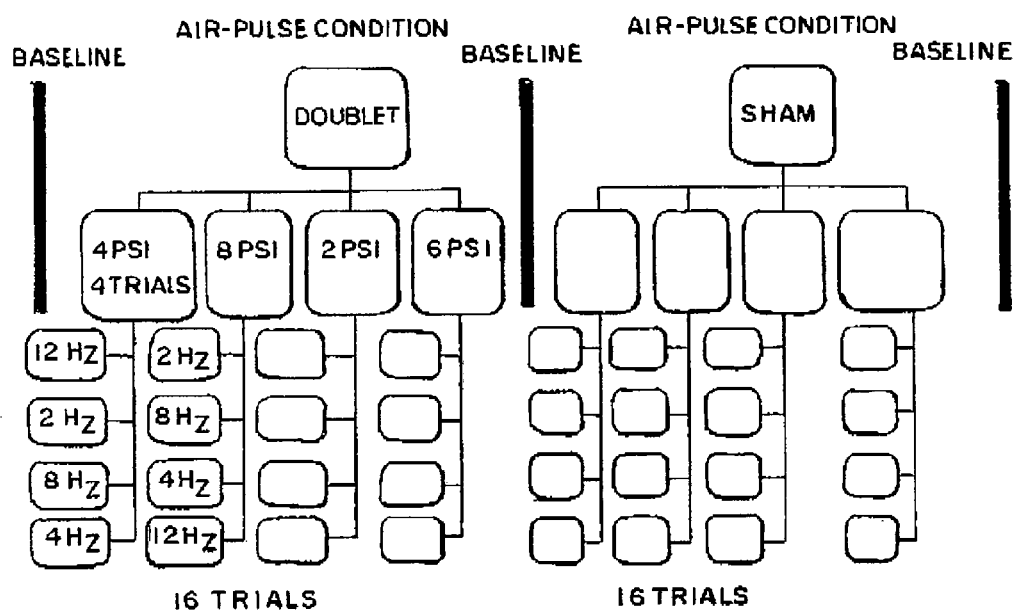
FIG. 8 is a schematic representation of the experimental protocols.

In the first of two experiments, twenty three (23) hospitalized individuals who had dysphagia secondary to a stroke volunteered as subjects. Their median age was 69, and 15 were male. The majority had suffered a stroke involving the right middle cerebral artery territory, however other stroke locations were also represented in the sample. The median days post-stroke at the time of testing was 12 days. Study enrolment was limited to patients who were dependent on tube feeding to some degree; thus, the median FOIS score for the sample was 1.5, with a range of 1 to 3. The experimental protocol is shown in FIG. 8.

Air-pulse trains were delivered bilaterally to the posterior oral cavity and oropharynx via a prototype buccal mouthpiece which was positioned between the subject's upper teeth and the cheek.

Figure 9:
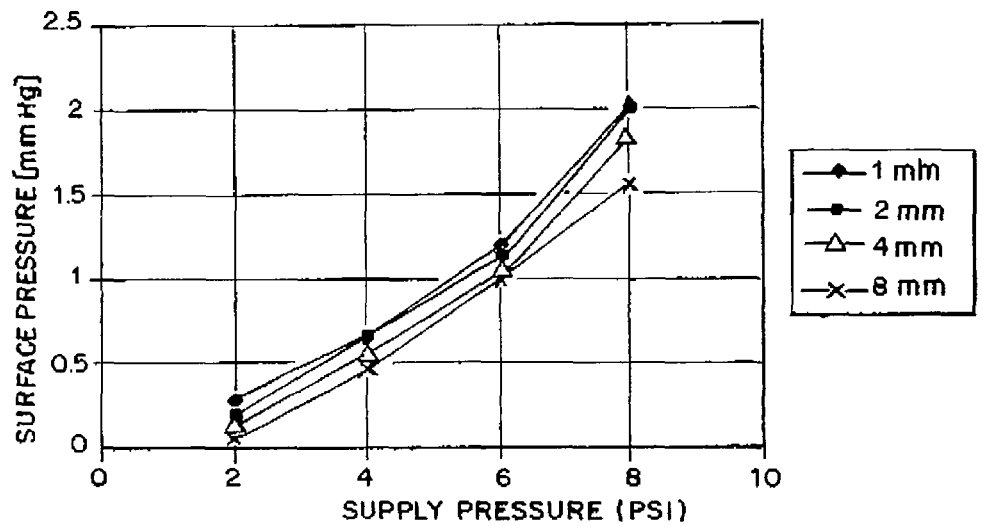
FIG. 9 is a graph showing the supply pressure versus the surface pressure as measured at a plurality of distances form the distal tip of the mouthpiece.

The air-pulse trains were controlled with an Agilent signal generator and LABneb air-pressure regulator, attached to a hospital wall-mounted compressed medical air source. We examined 4 levels of air-pulse train duration: a single pulse, a doublet or two successive pulses, a 2 second train, and a 3 second train; 4 levels of air-pulse amplitude were defined in terms of supply pressures of 2, 4, 6, and 8 psi; and finally, 4 levels of pulse frequency, 2, 4, 8, and 12 Hz, were examined. Based on bench testing, this range of supply pressures corresponded to tip pressures, measured 2 mm to 8 mm from the distal tip of the mouthpiece, of no greater than 2 mm Hg, as shown in FIG. 9.

Figure 10:
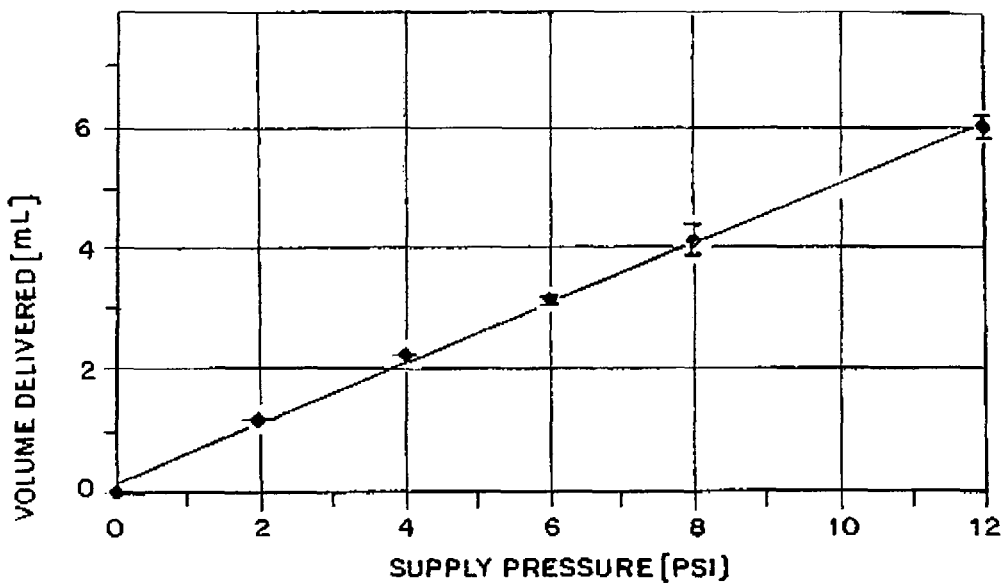
FIG. 10 is a graph showing supply pressure versus volume delivered for 5 ms pulse.

The air volume delivered with a single pulse in this supply pressure range was 1.2 ml to 4.2 ml, as shown by the tables provided below and the graph of FIG. 10.

| SINGLE | Volume Collected [mL] Source Pressure [psi] | | | | | |
|---|---|---|---|---|---|---|
| 50 ms | 0 | 2 | 4 | 6 | 8 | 12 |
| 1 Hz | 0 | 1.2 | 2.3 | 3.1 | 4.2 | 5.8 |
|  | 0 | 1.3 | 2.3 | 3.2 | 4.4 | 6.1 |
|  | 0 | 1.2 | 2.2 | 3.2 | 3.9 | 6 |
| Mean | 0.00 | 1.23 | 2.27 | 3.17 | 4.17 | 5.97 |
| SD | 0.00 | 0.06 | 0.06 | 0.06 | 0.25 | 0.15 |

|  | Volume Collected [mL] | | | |
|---|---|---|---|---|
| 2 Sec | 2 PSI | 4 PSI | 6 PSI | 8 PSI |
| 2 Hz | 3.8 | 7.5 | 12.1 | 15.6 |
|  | 4 | 7.4 | 11.8 | 15.8 |
|  | 4.2 | 7.7 | 11.9 | 15.5 |
| Mean | 4.00 | 7.53 | 11.93 | 15.63 |
| SD | 0.20 | 0.15 | 0.15 | 0.15 |
| 4 Hz | 6 | 14.4 | 23.5 | 31.4 |
|  | 6 | 15.1 | 23.7 | 31.6 |
|  | 6.1 | 14.5 | 23.4 | 30.8 |
| Mean | 6.03 | 14.67 | 23.53 | 31.27 |
| SD | 0.06 | 0.38 | 0.15 | 0.42 |
| 6 Hz | 12 | 25.1 | 36.4 | 45 |
|  | 11.8 | 25.2 | 36.3 | 47 |
|  | 11.6 | 24.8 | 36 | 48 |
| Mean | 11.80 | 25.03 | 36.23 | 46.67 |
| SD | 0.20 | 0.21 | 0.21 | 1.53 |
| 8 Hz | 14 | 32.4 | 50 | 62 |
|  | 14.1 | 32.7 | 49 | 62 |
|  | 13.7 | 32.8 | 50 | 62 |
| Mean | 13.93 | 32.63 | 49.67 | 62.00 |
| SD | 0.21 | 0.21 | 0.58 | 0.00 |
| 12 Hz | 20.6 | 44 | 68 | 90 |
|  | 20.4 | 46 | 68 | 89 |
|  | 20.7 | 46 | 68 | 90 |
| Mean | 20.57 | 45.33 | 68.00 | 89.67 |
| SD | 0.15 | 1.15 | 0.00 | 0.58 |

|  | Volume Collected [mL] | | | |
|---|---|---|---|---|
| 3 Sec | 2 PSI | 4 PSI | 6 PSI | 8 PSI |
| 2 Hz | 5 | 12 | 22 | 26 |
|  | 4 | 12 | 22 | 28 |
|  | 4 | 12 | 22 | 27 |
| Mean | 4.33 | 12.00 | 22.00 | 27.00 |
| SD | 0.58 | 0.00 | 0.00 | 1.00 |
| 4 Hz | 8 | 28 | 38 | 48 |
|  | 8 | 27 | 38 | 50 |
|  | 8 | 29 | 36 | 50 |
| Mean | 8.00 | 28.00 | 37.33 | 49.33 |
| SD | 0.00 | 1.00 | 1.15 | 1.15 |
| 6 Hz | 14 | 36 | 54 | 70 |
|  | 18 | 38 | 54 | 70 |
|  | 16 | 38 | 55 | 68 |
| Mean | 16.00 | 37.33 | 54.33 | 69.33 |
| SD | 2.00 | 1.15 | 0.58 | 1.15 |
| 8 Hz | 20 | 44 | 70 | 90 |
|  | 22 | 46 | 72 | 92 |
|  | 24 | 46 | 72 | 90 |

-continued

| 3 Sec | Volume Collected [mL] | | | |
|---|---|---|---|---|
| | 2 PSI | 4 PSI | 6 PSI | 8 PSI |
| Mean | 22.00 | 45.33 | 71.33 | 90.67 |
| SD | 2.00 | 1.15 | 1.15 | 1.15 |
| 12 Hz | 30 | 62 | 92 | 130 |
| | 28 | 62 | 92 | 130 |
| | 29 | 60 | 94 | 130 |
| Mean | 29.00 | 61.33 | 92.67 | 130.00 |
| SD | 1.00 | 1.15 | 1.15 | 0.00 |

Pulse duration was 50 msec throughout.

Air pulse types were presented in blocks of train duration and sham conditions, that is, there were a total of 5 blocks: single pulse, doublet, 2-sec pulse train, 3-sec pulse train, and sham, two of which are shown here. Successive duration blocks were separated by a 1 min baseline period.

Their order was randomized across subjects. The four air-pulse amplitude conditions were nested as blocks within train duration; and the four levels of air-pulse frequency were further nested within amplitude blocks. There were two orders of each of the amplitude and frequency conditions across subjects. The duration between the onsets of successive pulse trains was approximately 20 sec.

During the sham condition, the air pressure regulator was turned to "0" but the signal generator operated such that the subjects, and experimenters, heard the same noise of the solenoids during the air-pulse and sham conditions.

Dry swallows were identified from the output signals of a Grass throat microphone, a laryngeal movement sensor, and respiratory movement sensor. Two swallows are shown here in relation to three single air-pulse trials. One experimenter observed the subject throughout the session and marked the computer file for swallows and other behaviors. Swallowing rates were computed as number of swallows over duration of the air-pulse condition, from the onset of 1 trial to the onset of the following trial.

Figure 11:
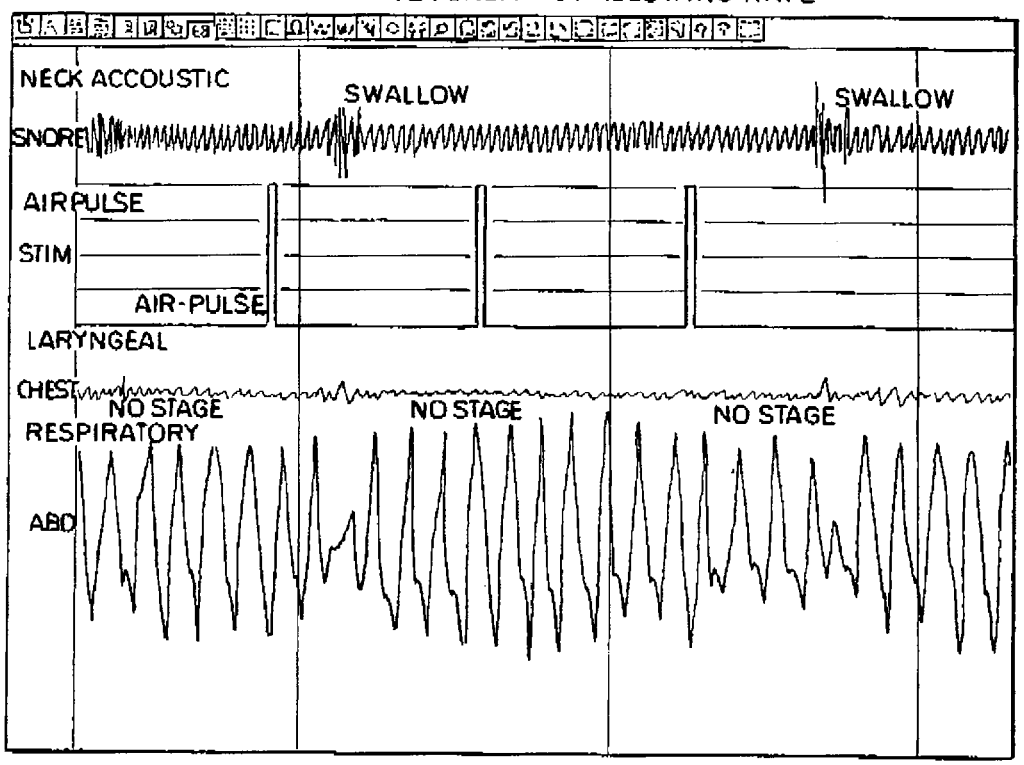
FIG. 11 is a graph showing the saliva swallowing rate.

A repeated measures 1-way ANOVA indicated that there was a main effect of Train Duration on saliva swallowing rate ($p<0.05$). Post-hoc comparisons, with Bonferroni correction, indicated that mean swallowing rates associated with the 2 sec, and the 3 sec train duration conditions were significantly greater than the mean swallowing rate associated with the single pulse condition ($p<0.008$) as shown in FIG. 11.

Figure 12:
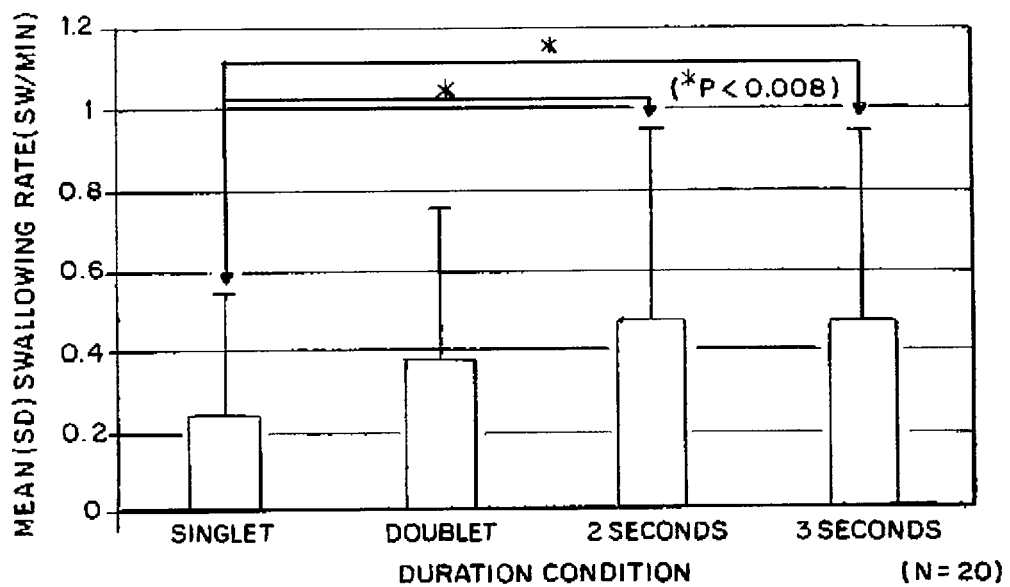
FIG. 12 is a graph showing the effect of air-pulse train duration.
Figure 13:
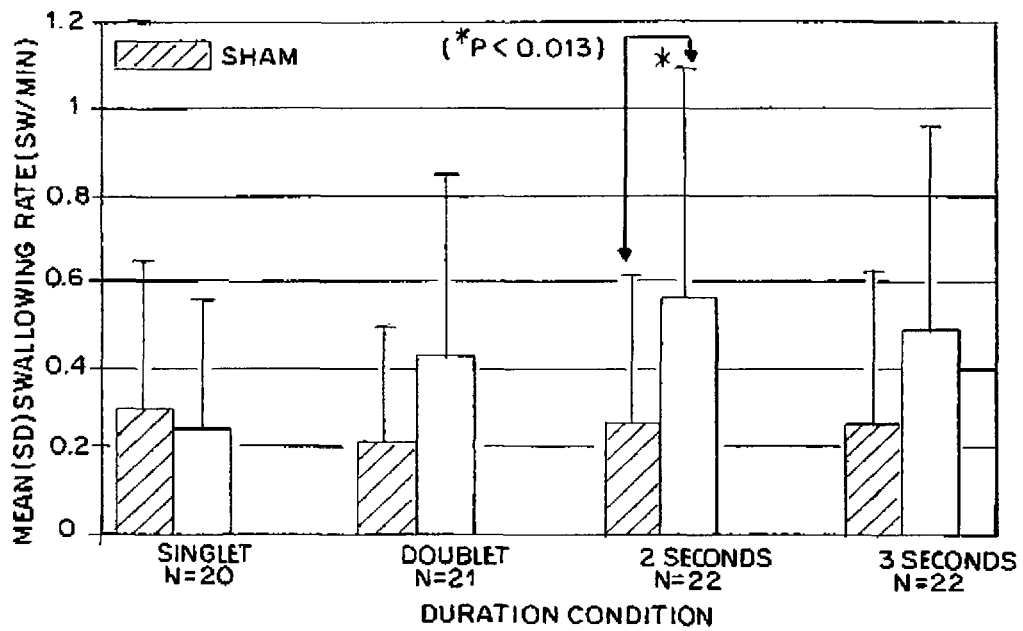
FIG. 13 is a graph showing air-pulse train duration versus sham.

In relation to the sham condition, paired t-tests, again Bonferroni corrected, indicated that the mean swallowing rate associated with the 2 sec train duration condition was significantly greater than the swallowing rate associated with the sham condition ($p<0.013$) as shown in FIGS. 12 and 13.

Figure 14:
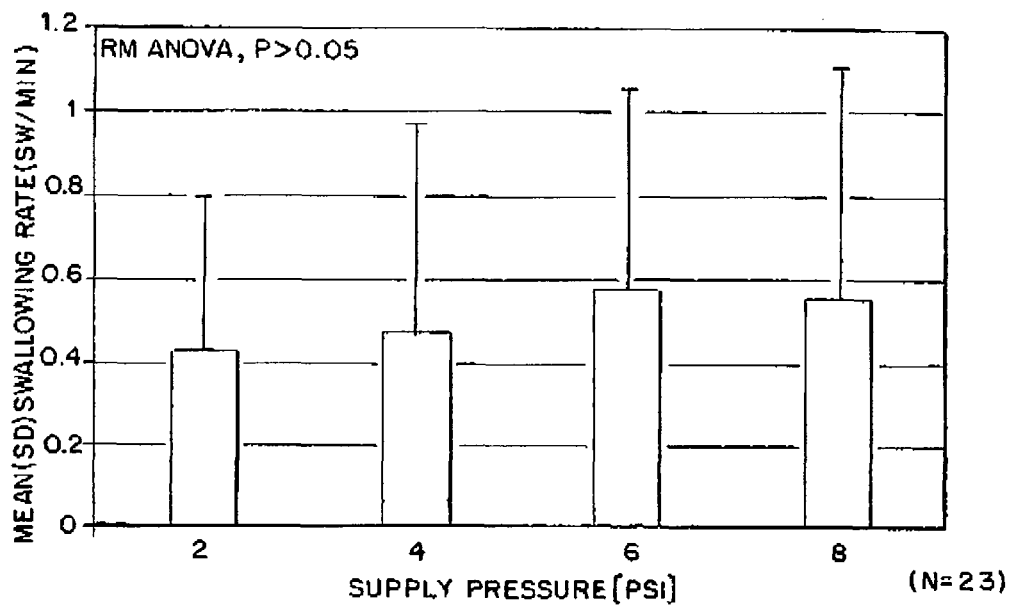
FIG. 14 is a graph showing the effect of air-pulse amplitude.
Figure 15:
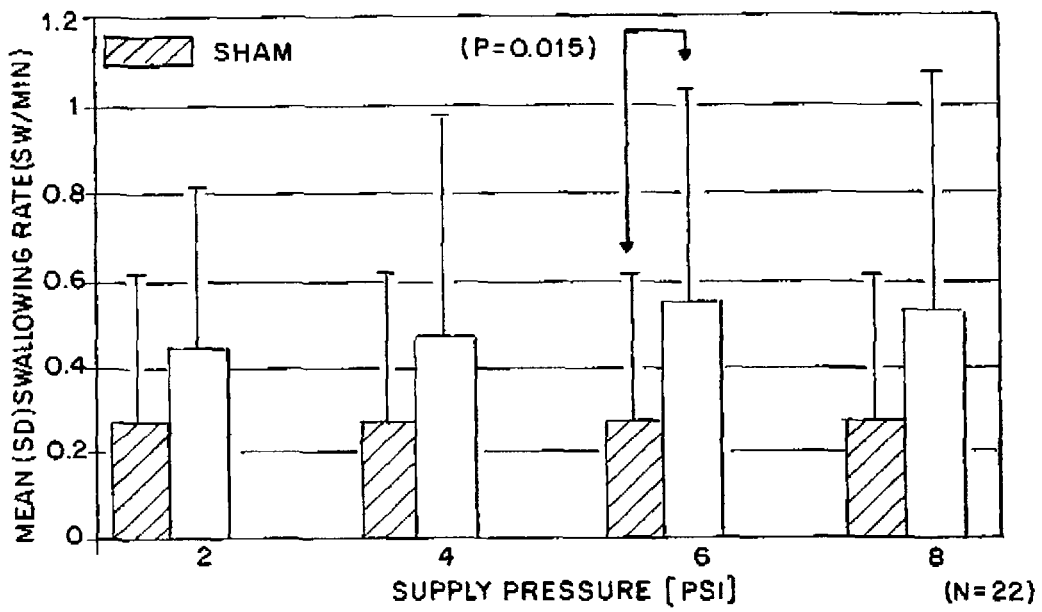
FIG. 15 is a graph showing air-pulse amplitude versus sham.

Turning now to air-pulse amplitude, there was no main effect of air-pulse AMPLITUDE on dry swallowing rate. Compared with the SHAM condition, the 6 psi condition approached the corrected significance level of 0.013 ($p=0.015$). And, the average swallowing rate across the 4 levels of amplitude was significantly greater than the mean swallowing rate associated with the SHAM condition ($p<0.05$) as shown in FIGS. 14 and 15.

Figure 16:
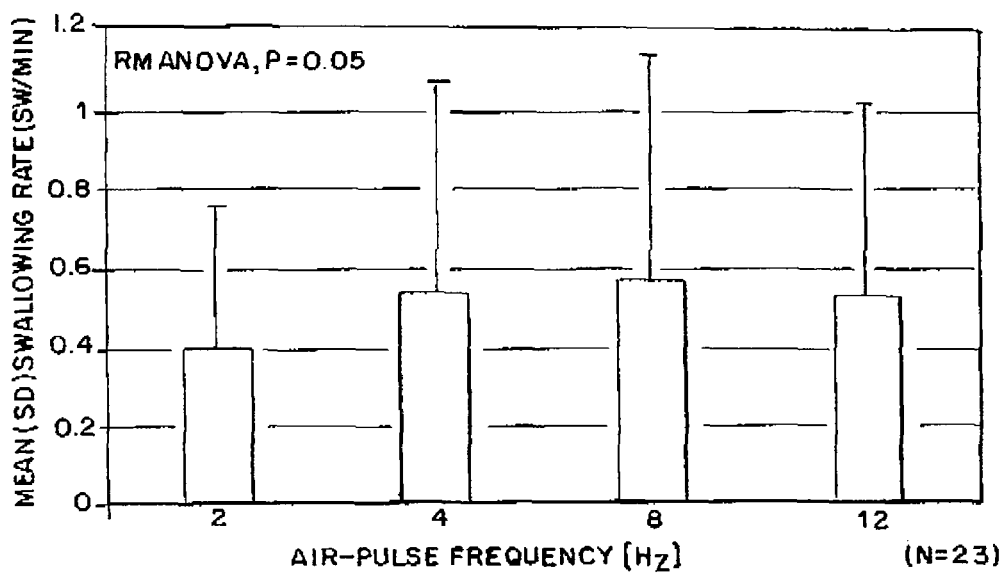
FIG. 16 is a graph showing the effect of air-pulse frequency.
Figure 17:
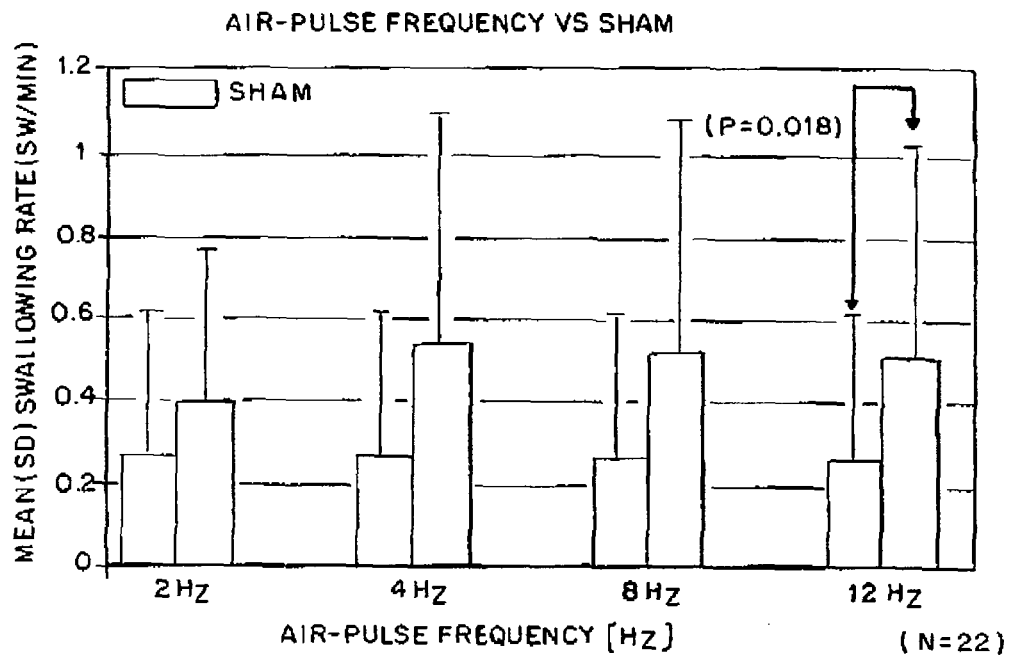
FIG. 17 is a graph showing air-pulse frequency versus sham.

Looking now at air-pulse frequency, there was no mean effect of air-pulse FREQUENCY on dry swallowing rate. Compared with the SHAM condition, the 12 Hz condition approached the corrected significance level ($p=0.018$). The average swallowing rate across the 4 levels of air-pulse frequency was significantly greater than the mean swallowing rate associated with the SHAM condition ($p<0.05$) as shown in FIGS. 16 and 17.

For the air-pulse Duration, Amplitude and Frequency conditions examined, there was considerable variability in dry swallowing rates, as illustrated by the large standard deviations.

In summary, it was determined that swallowing rates showed substantial variability for the air-pulse types examined. Longer air-pulse trains were associated with greater swallowing rates compared with single pulses; swallowing rates associated with 2 sec air-pulse trains were significantly greater than sham. While swallowing rates were not significantly different as a function of air-pulse (i) amplitude, and (ii) frequency conditions, swallowing rates pooled across amplitude or frequency levels were significantly greater than sham. Air-pulse trains, delivered to the posterior mouth and oropharynx via a buccal mouthpiece, were associated with increased saliva swallowing rates in dysphagic stroke.

Dry swallowing rates are influenced by the specific properties of air-pulse trains delivered to the posterior mouth and oropharynx in dysphagia stroke. Air-pulse application is associated with increased dry swallowing rates in dysphagic stroke, supporting the potential of the air-pulse approach in swallowing rehabilitation.

Although there were some significant effects of the air-pulse parameters under study, the effects of air-pulse frequency and amplitude were not marked. With regards to pulse-train duration, the 2-second pulse train appears to be superior to the other pulse types in terms of facilitating swallowing in patients with dysphagia. However, even in the case of duration, there was not a single setting that proved to be categorically superior to the others in terms of associated swallowing rates. This suggests that air pulses that fall within a range of pulse types can be associated with increased swallowing in patients with swallowing impairment. This is an advantage of the air-pulse approach in that the phenomenon does not appear to be limited to a very narrow set of pulse types.

The present finding that air-pulse amplitude and frequency did not have more pronounced effects on swallowing rates suggests the possibility that factors other than air pressure may be important in determining the swallowing response.

Based on this study, air-pulse trains of 2 sec appear to be particularly effective in evoking swallowing in patients with dysphagia following brain injury. Air-pulse trains involving a supply pressure of 6 psi, and involving a frequency of 12 Hz, i.e., involving flow values in the range of 68 mls, also appear to be particularly effective, based on the current testing results in dysphagic patients.

This study demonstrates that oropharyngeal air-pulse trains delivered via a buccal mouthpiece and involving tip pressures (i.e., measured at 2 mm to 8 mm from the tip through bench testing) of less than or equal to 2 mm Hg are effective in increasing saliva swallowing rates in patients with dysphgia following stroke.

The subjects in the current study participated in testing sessions that were approximately 75 minutes in duration. During that period, air-pulse trains were delivered for a period of approximately 20 minutes in 6 minute blocks based on air-pulse train duration, the order of which was randomized across subjects. Subjects were observed to swallow during the various air-pulse duration blocks. There was no trend for swallowing to decrease over the course of the testing session. Based on this experience, an air-pulse application period of approximately 20 minutes is appropriate and preferred in terms of increasing swallowing rates in patients with dysphgia following stroke.

The time between successive air-pulse trains should be (i) short enough that the patient receives an adequate number of bursts per session, but (ii) long enough that the patient does not risk desaturation because of an excessive number of swallowing apneas. Based on the experiment described above, preferred air pulse trains of bursts of 2 sec, 6 psi and 12 Hz, and an inter-stimulus time of 20 sec, the mean+1 sd swallowing rate is less that 3 per min.

Therefore, even patients who respond quite well to the air pulses would not be expected to swallow more than 3 times per minute with an interburst time of 20 sec. A swallowing rate of 3 per min is less than typical swallowing rates for cup drinking, or mealtime eating. Based on this logic, a 20 sec period between the onsets of successive air-pulse trains may be appropriate and thus preferred.

Figure 18:
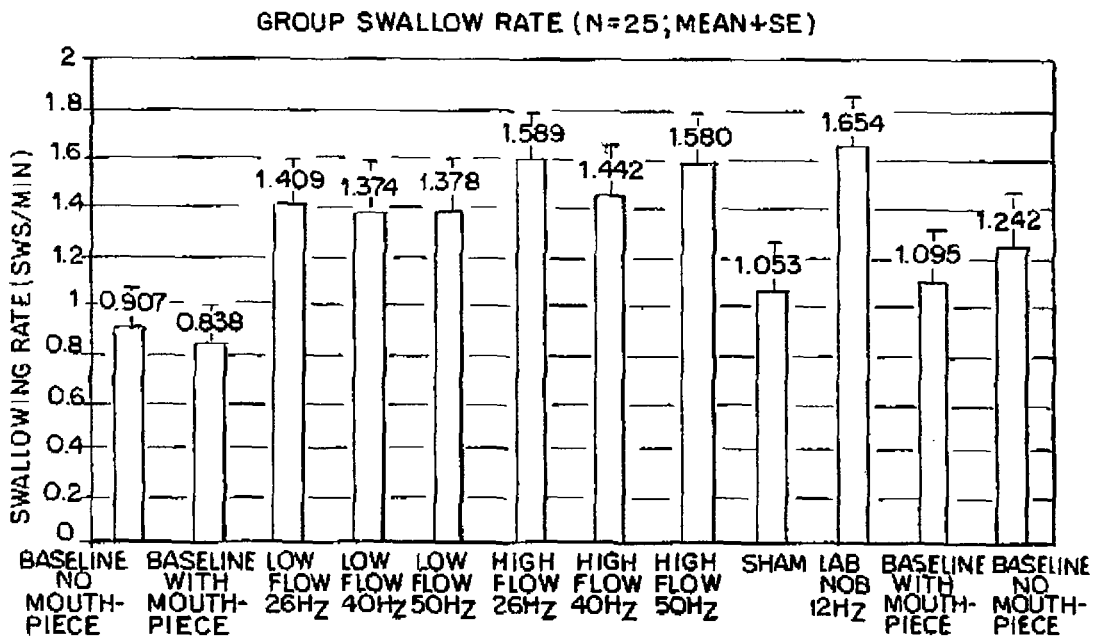
FIG. 18 is a histogram showing the group swallowing rates.
Figure 19:
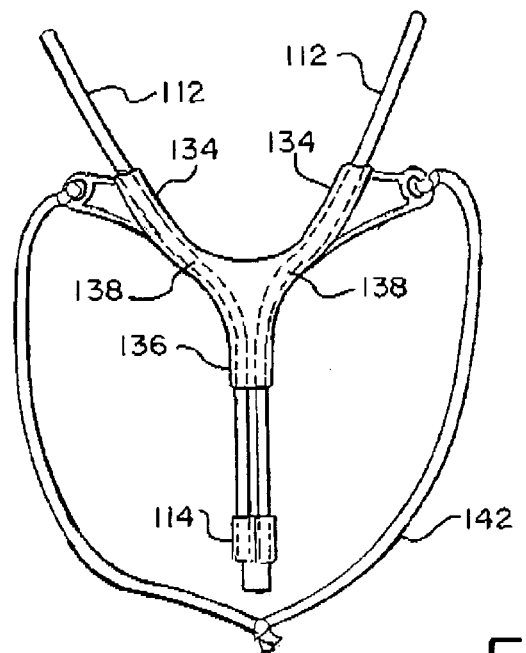
FIG. 19 is a plan view of an alternative embodiment oral device.
Figure 21:
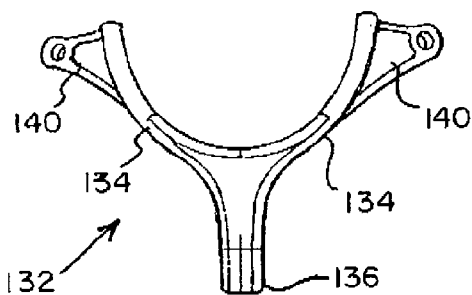
FIG. 21 is a front view of the yoke shown in FIG. 20.

Based on our finding that air-pulse trains of 12 Hz are particularly effective, as well as our hypotheses on air flow, a second study was designed to examine higher frequencies, and different air flows, as follows: Oropharyngeal air pulses in the 2 to 12 Hz range are associated with increased swallowing rates in controls and dysphagic patients. However, the effects of higher frequency air pulses, and air flow, are unknown. Therefore, the effects of oropharyngeal air-pulse frequency, and air flow on dry swallowing rates in healthy adults was examined, and compared with a lower frequency air-pulse train employed previously. Methods: Air-pulse trains (duration=3 sec) were delivered to the oropharynx via a prototype buccal over-the-ear mouthpiece in 25 adults (mean±sd age: 26.7±7.9 years; 18 female). Laryngeal, respiratory, and acoustic signals were recorded while six air-pulse conditions were randomly administered to each subject: three Frequency conditions (i.e., 26 Hz, 40 Hz, 59 Hz); crossed with two Flow conditions (i.e., Low Air Flow, High Air Flow) as shown in FIG. 18. A Sham condition, and an 8 Hz air-pulse train previously associated with swallowing, were also examined. Results: While main effects of Frequency, Air Flow, and the Frequency×Air-Flow interaction were not statistically significant (Repeated Measures 2-way ANOVA, pcrit<0.05), Air Flow approached significance (pobs=0.056). When the data were averaged across Frequency conditions, the mean swallowing rate during the 8 Hz condition was significantly greater than that during the Low Flow condition; however, the 8 Hz and High Flow conditions were not significantly different (paired t-test, pcrit<0.025). Moreover, swallowing rates during the High Flow and 8 Hz conditions were significantly greater than the Sham swallowing rate, whereas the Low Flow and Sham conditions were not significantly different (paired t-test, pcrit<0.016). Conclusion: Oropharyngeal air-pulse trains delivered across a range of frequencies, particularly at higher air flows, increase dry swallowing rates in healthy adults, supporting their potential in dysphagia rehabilitation.

In addition to increased dry swallowing during the air-pulse application periods, some subjects were observed to display increased overall arousal, and increased overall motor behaviour, in relation to the air-pulse application. For example, some patients opened their eyes, moved their arms and legs, changed position in their chair, etc, in relation to the air-pulse application. Based on the observation, air-pulse application to the back of the mouth and/or the oropharynx appears to provide a method on increasing overall arousal in individuals with brain damage, and further appears to provide a method of increasing motor behaviour in individuals with brain damage. These methods are particularly important in patients with brain damage, for example, in stroke, where decreased arousal and lack of motor behaviour can be significant challenges during the stroke recovery period that may limit gains in rehabilitation. Thus, the air-pulse approach may be employed in the rehabilitation of patients with brain injury, or possibly dementia, to increase arousal and motor behaviour, in addition to increasing swallowing.

The increased arousal and motor behaviour observed in patients with stroke in association with air-pulse application to the posterior mouth and oropharynx in consistent with our previous finding that oropharyngeal air-pulse application activates the cerebral cortex in healthy control subjects. Various aspects of those findings are further disclosed in U.S. Publication No. 2010/0010400A1, entitled Method of Brain Activation, the entire disclosure of which is hereby incorporated herein by reference. Therefore, for example, cortical activation secondary to air-pulse application may mediate the increases in arousal and motor behaviour observed among stroke patients in the current study.

Generally speaking, the systems described herein are directed to oral mouthpieces. As required, embodiments of the present invention are disclosed herein. However, the disclosed embodiments are merely exemplary, and it should be understood that the invention may be embodied in many various and alternative forms. The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to oral mouthpieces.

As used herein, the terms "comprises" and "comprising" are to construed as being inclusive and open ended rather than exclusive. Specifically, when used in this specification including the claims, the terms "comprises" and "comprising" and variations thereof mean that the specified features, steps or components are included. The terms are not to be interpreted to exclude the presence of other features, steps or components.

What is claimed is:

1. An oral mouthpiece comprising:
   an intraoral portion defining an intraoral conduit having at least one outlet port adapted to dispense at least one fluid pulse;
   an extraoral portion integrally formed with the intraoral portion, the extraoral portion defining an extraoral conduit in flow communication with the intraoral conduit, the extraoral portion being connectable to a fluid supply wherein the intraoral portion and extraoral portion form a delivery conduit, and wherein the intraoral portion meets the extraoral portion in a pair of first loop regions such that each first loop region is adapted to be positioned at a corner of a user's mouth; and
   an auxiliary support device coupled to the extraoral portion, wherein the auxiliary support device is formed separately from the intraoral and extraoral portions and comprises a different material than the intraoral and extraoral portions, wherein the auxiliary support device comprises a pair of ear connectors, and wherein the extraoral portion further includes a pair of second loop regions, each of the second loop regions spaced cheekwardly from a corresponding one of the first loop regions and wherein each of the pair of ear connectors is connected to a respective second loop region.

2. The oral mouthpiece as claimed in claim 1 wherein the extraoral portion includes a pair of chin portions extending downwardly from each of the pair of second loop region.

3. The oral mouthpiece as claimed in claim 2 wherein the pair of chin portions meet and are in flow communication with the supply.

4. The oral mouthpiece as claimed in claim 2 wherein the pair of chin portions meet in an adjustable Y-connector.

5. The oral mouthpiece as claimed in claim 1 wherein the intraoral portion extends from a centre to each side of a user's mouth.

6. The oral mouthpiece as claimed in claim 5 wherein a single extraoral portion extends outwardly from the intraoral portion.

7. The oral mouthpiece as claimed in claim 5 wherein the auxiliary support device is connected to the single extraoral portion.

8. An oral mouthpiece comprising:
   an intraoral portion defining an intraoral conduit having at least one outlet port adapted to dispense at least one fluid pulse;
   an extraoral portion integrally formed with the intraoral portion, the extraoral portion defining an extraoral conduit in flow communication with the intraoral conduit, the extraoral portion being connectable to a fluid supply whereby the intraoral portion and extraoral portion form a delivery conduit; and
   an auxiliary support device coupled to the extraoral portion, wherein the auxiliary support device is formed separately from the intraoral and extraoral portions and comprises a different material than the intraoral and extraoral portions, wherein said auxiliary support device comprises a pair of ear connectors, wherein each ear connector is an ear loop, and wherein each ear loop comprises a knitted material.

9. An oral mouthpiece comprising:
   an intraoral portion defining an intraoral conduit having at least one outlet port adapted to dispense at least one fluid pulse;
   an extraoral portion integrally formed with the intraoral portion, the extraoral portion defining an extraoral conduit in flow communication with the intraoral conduit, the extraoral portion being connectable to a fluid supply whereby the intraoral portion and extraoral portion form a delivery conduit; and
   an auxiliary support device coupled to the extraoral portion, wherein the auxiliary support device is formed separately from the intraoral and extraoral portions and comprises a different material than the intraoral and extraoral portions, wherein the auxiliary support device comprises a laterally extending support member positioned above the extraoral portion and adapted to engage the user's face above an upper lip, and at least one securing member separate from the extraoral portion coupled to opposite ends of the support member.

10. The oral mouthpiece of claim 9 wherein the at least one securing member comprises a band.

11. The oral mouthpiece of claim 10 wherein the band comprises an ear loop.

12. An oral mouthpiece comprising:
    an intraoral portion defining an intraoral conduit having at least one outlet port adapted to dispense at least one fluid pulse;
    an extraoral portion integrally formed with the intraoral portion, the extraoral portion defining an extraoral conduit in flow communication with the intraoral conduit, the extraoral portion being connectable to a fluid supply whereby the intraoral portion and extraoral portion form a delivery conduit; and
    an auxiliary support device coupled to the extraoral portion, wherein the auxiliary support device is formed separately from the intraoral and extraoral portions and comprises a different material than the intraoral and extraoral portions, wherein the auxiliary support device comprises a yoke and at least one securing member separate from the extraoral portion connected to the yoke.

13. The oral mouthpiece as claimed in claim 12 wherein the yoke comprises a Y-shaped frame supporting the extraoral portion and a pair of attachment members positioned on opposite sides of the frame, wherein the at least one securing member is connected to the attachment members.

14. An oral mouthpiece comprising:
    an intraoral portion defining an intraoral conduit having at least one outlet port adapted to dispense at least one fluid pulse;
    an extraoral portion integrally formed with the intraoral portion, the extraoral portion defining an extraoral conduit in flow communication with the intraoral conduit, the extraoral portion being connectable to a fluid supply whereby the intraoral portion and extraoral portion form a delivery conduit; and an auxiliary support device coupled to the extraoral portion, wherein the auxiliary support device is formed separately from the intraoral and extraoral portions and comprises a different material than the intraoral and extraoral portions, wherein the auxiliary support device comprises a U-shaped frame shaped separate from the extraoral portion and configured to engage the user's chin, the frame having opposite end portions coupled to the extraoral portion.

15. The oral mouthpiece of claim 14 further comprising at least one securing member coupled to the opposite end portions, wherein the at least one securing member comprises a band.

16. An oral mouthpiece comprising:
    a pair of laterally spaced intraoral portions defining intraoral conduits each having at least one outlet port adapted to dispense at least one fluid pulse; and
    an extraoral portion integrally formed with each of the intraoral portions, the extraoral portions defining extraoral conduits in flow communication with the intraoral conduits, the extraoral portions being connectable to a fluid supply wherein the intraoral portions and extraoral portions form a delivery conduit, wherein the extraoral portions comprise a pair of spaced apart lip bends communicating with the intraoral portions and a pair of chin portions extending downwardly from the lip bends, the chin portions forming a loop positionable under the user's chin.

17. The oral mouthpiece as claimed in claim 16 further comprising an auxiliary support device coupled to the extraoral portion, wherein the auxiliary support device is formed separately from the intraoral and extraoral portions and comprises a different material than the intraoral and extraoral portions.

18. The oral mouthpiece as claimed in claim 17 wherein said auxiliary support device comprises an ear loop band.

* * * * *